United States Patent
Thompson et al.

(10) Patent No.: US 7,964,636 B2
(45) Date of Patent: Jun. 21, 2011

(54) SYNTHESIS AND USE OF NOVEL INHIBITORS AND INACTIVATORS OF PROTEIN ARGININE DEIMINASES

(75) Inventors: Paul Ryan Thompson, Columbia, SC (US); Yuan Luo, Dallas, TX (US)

(73) Assignee: University of South Carolina, Columbia, SC (US)

( * ) Notice: Subject to any disclaimer, the term of this patent is extended or adjusted under 35 U.S.C. 154(b) by 495 days.

(21) Appl. No.: 12/092,627

(22) PCT Filed: Nov. 7, 2006

(86) PCT No.: PCT/US2006/043378
§ 371 (c)(1),
(2), (4) Date: Sep. 19, 2008

(87) PCT Pub. No.: WO2007/056389
PCT Pub. Date: May 18, 2007

(65) Prior Publication Data
US 2009/0306153 A1 Dec. 10, 2009

Related U.S. Application Data

(60) Provisional application No. 60/734,339, filed on Nov. 7, 2005, provisional application No. 60/791,259, filed on Apr. 12, 2006, provisional application No. 60/818,561, filed on Jul. 5, 2006.

(51) Int. Cl.
*A61K 31/35* (2006.01)

(52) U.S. Cl. ........................................................ 514/454
(58) Field of Classification Search ................... 514/454
See application file for complete search history.

(56) References Cited

OTHER PUBLICATIONS

Kearney et al., "Kinetic Characterization of Protein Arginine Deiminase 4: A Transcriptional Corepressor Implicated in the Onset and Progression of Rheumatoid Arthritis", Biochemistry, vol. 44, No. 31, pp. 10570-10582, (2005).
Luo, Y. et al., "A Fluoroacetamidine-Based Inactivator of Protein Arginine Deiminase 4: Design, Synthesis, and in Vitro and in Vivo Evaluation", J. Am. Chem. Soc., vol. 128, No. 4, pp. 1092-1093, (2006).
Luo, Y. et al., "Inhibitors and Inactivators of Protein Arginine Deiminase 4: Functional and Structural Characterization", Biochemistry, vol. 45, No. 39, pp. 11727-11736, (2006).
Luo, Y. et al., "Activity-Basted Protein Profiling Reagents for Protein Arginine Deiminase 4 (PAD4): Synthesis and in vitro Evaluation of a Fluorescently Labeled Probe", J. Am. Chem. Soc., vol. 128, No. 45, pp. 14468-14469, (2006).
Thompson et al., "Histone Citrullination by Protein Arginine Deiminase: Is Arginine Methylation a Green Light or a Roadblock?", ACS Chemical Biology, vol. 1, No. 7, pp. 433-441, (2006).

*Primary Examiner* — Raymond J Henley, III
(74) *Attorney, Agent, or Firm* — Dority & Manning, P.A.

(57) ABSTRACT

In one embodiment of the present disclosure, an inactivator of protein arginine deiminase 4 is disclosed. The inactivator includes: (I) and x includes F; Cl, and H, y includes OH and $NH_2$, R includes H, an alkyl group, an alkenyl group, an alknyl group, and n is greater than 0.

24 Claims, 24 Drawing Sheets

1: X = H, Y = OH
2: X = F, Y = NH$_2$
3: X = Cl, Y = NH$_2$

Figure 1. Structures of (halo)amidine-based PAD4 inhibitors and inactivators that have been synthesized and tested. The structure of benzoyl arginine amide (BAA), a PAD substrate, is displayed here for comparison.

Figure 2

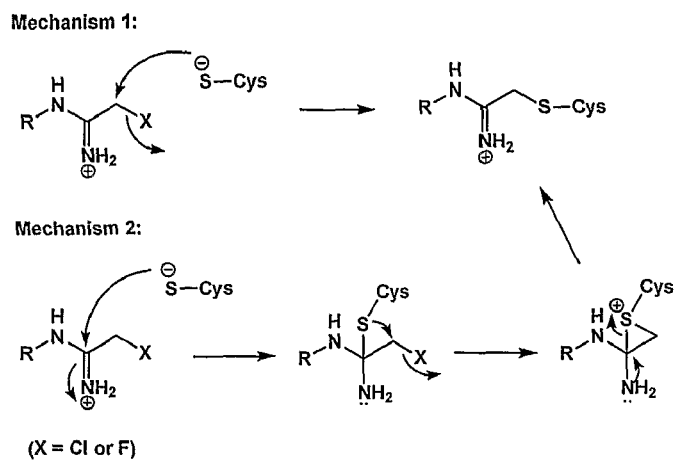

Figure 2. Two potential mechanisms of PAD inactivation by compounds 2-3. Mechanism 1 involves direct substitution of the halide; whereas mechanism 2 involves the formation of a tetrahedral intermediate, which first evolves into a three-membered sulfonium ring and subsequently rearranges to form the thioether. The second mechanism is typically invoked to account for the poor leaving group potential of fluoride.

R could be other substituents that are not included here, such as alkyl, alkenyl and alknyl groups. R could be at p-, m- or o- position of the benzene ring.

Figure 3. Structures of other (halo)amidine-based PAD4 inhibitors/inactivators. Compounds 15 and 19 have been synthesized and their $IC_{50}$'s are 6.67 ± 0.33 (µM) and 25.54 ± 5.57 (µM), respectively.

Figure 4. Inhibitor concentration-PAD4 activity data obtained by $IC_{50}$ assays of 1 (H-amidine), 2 (F-amidine), and 3 (Cl-amidine). The assay buffers containing 10 mM $CaCl_2$, 250 μM TCEP were pre-incubated with PAD4 (0.2 μM for compound 1 and 0.5 μM for compound 2-3) at 37°C for 10 min; reactions were initiated by addition of 1 mM BAEE, and then incubated at 37°C for 20 min.

Figure 5

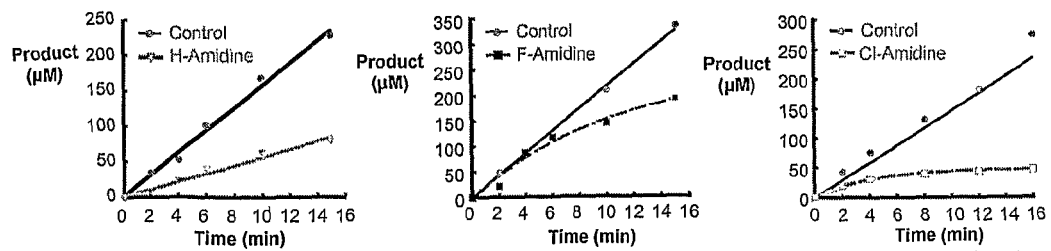

Figure 5. Time course of inhibition. Plots of product formation versus time are depicted in the absence (○) and presence of either H-Amidine (△; left), F-Amidine (■; middle), or Cl-Amidine (□; right). The compound 1 (H-Amidine; 25 mM final) and compound 2 (F-Amidine; 500 μM final) time courses were performed in the presence of 10 mM benzoyl Arg ethyl ester (BAEE) and 10 mM CaCl$_2$; whereas the compound 3 (Cl-Amidine; 50 μM final) time course was performed in the presence of 1 mM BAEE and 10 mM CaCl$_2$.

Figure 6. Lineweaver-Burk transformation of substrate concentration-rate data obtained from kinetic assays for PAD4 in the presence of compound 1—H-amidine at varying concentrations (0 (♦), 5 ( ), 10 (△) mM).

Figure 7

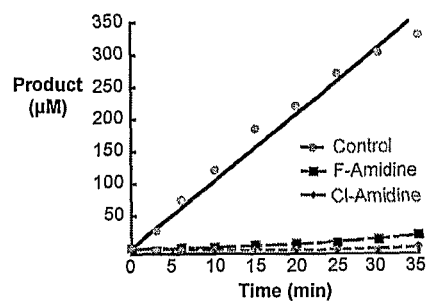

Figure 7. Rapid dilution time course experiments. The recovery of PAD4 activity was determined by rapidly diluting pre-formed PAD4·inhibitor complexes 95-fold (1.75 μM final) into assay buffer containing 10 mM BAEE. At the indicated time points, product formation was detected using our assay for Cit production. PAD4·inhibitor complexes were generated by incubating PAD4 with 167 μM of either compound 2—F-amidine (■) or compound 3-Cl—Amidine (♦) for 30 min at 37 °C. Control assays (○) were treated identically.

Figure 9

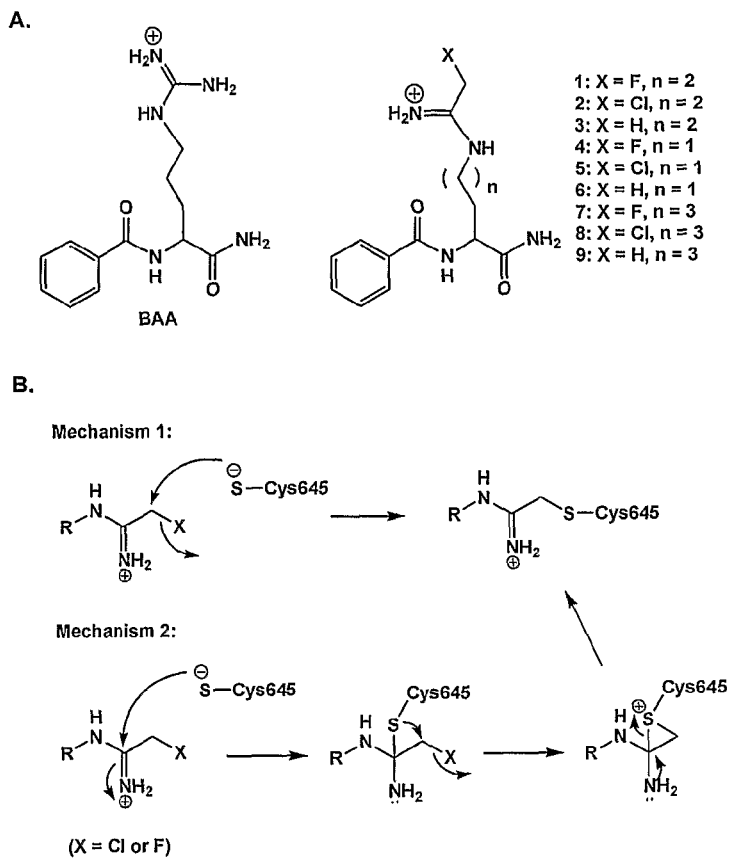

Figure 9. Structures of (halo)acetamidine-based PAD4 inhibitors/inactivators and potential mechanisms of inactivation. A. The structure of BAA and the (halo)acetamidine-based inhibitors and inactivators of PAD4. B. Two potential mechanisms of PAD4 inactivation. Mechanism 1 involves direct substitution of the halide; whereas mechanism 2 involves the formation of a tetrahedral intermediate, which first evolves into a three-membered sulfonium ring and subsequently rearranges to the thioether with the collapse of the tetrahedral intermediate. The latter mechanism is invoked to account for the poor leaving group potential of fluoride.

Figure 10

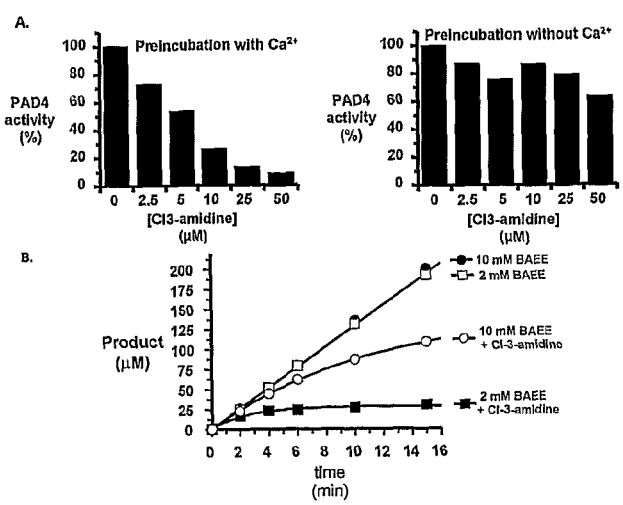

Figure 10. Calcium and substrate dependence of Cl3-amidine induced inactivation. A. PAD4 was pre-incubated with increasing concentrations of Cl3-amidine in the absence and presence of calcium and then BAEE added to initiate the $IC_{50}$ assay. Calcium was also added at this time to the sample pre-incubated in the absence of this metal ion to upregulate the activity of PAD4. B. Substrate protection was assayed by observing the time dependent inactivation properties of Cl3-amidine (100 μM). For these studies, product formation in the presence and absence of Cl3-amidine was quantified as a function of time using two different concentrations of BAEE (2 and 10 mM) as the substrate.

Figure 11

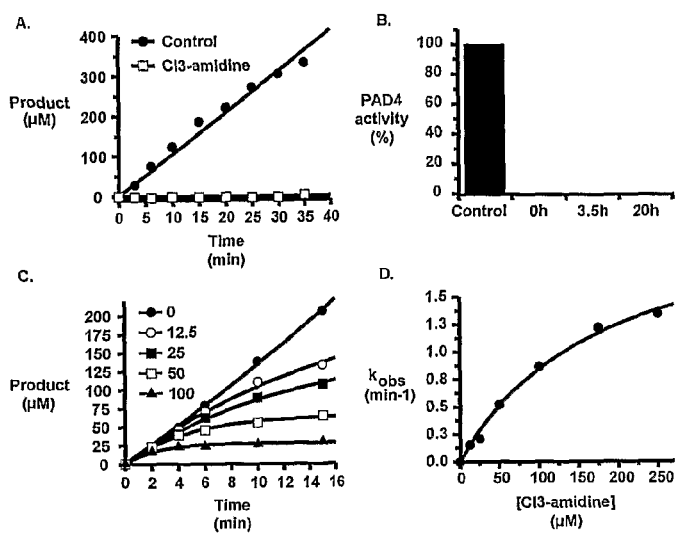

Figure 11. Cl3-amidine is an irreversible time- and concentration-dependent inactivator of PAD4. A Rapid dilution of the preformed PAD4•Cl3-amidine, and controls containing no inhibitor, into assay buffer containing excess substrate did not show any recovery of activity. B. Dialysis of preformed PAD4•Cl3-amidine complexes for 0, 3.5, and 20 h did not show any recovery of activity. C. Plots of product formation over time in the absence and presence of increasing concentrations (12.5, 25, 50, and 100 μM) of Cl3-amidine. D. Plot of $k_{obs}$ versus the concentration of Cl3-amidine.

Figure 12

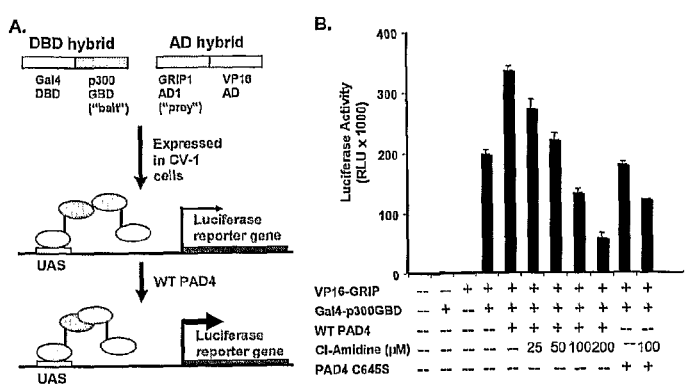

Figure 12. Cl3-amidine inhibits the PAD4 mediated enhancement of the p300GBD-GRIP1 interaction in CV-1 cells. A. Schematic depiction of the mammalian two-hybrid assay used to evaluate the efficiency of the p300GBD-GRIP1 interaction. B. CV-1 cells were transfected with a luciferase reporter construct as well as plasmids encoding the proteins depicted in this panel. The indicated concentrations of Cl3-amidine were added to the cell culture medium and incubated for 40 hours. Cell extracts were then prepared and the luciferase activity present in these extracts quantified. The catalytically defective PAD4 C645S mutant was also transfected into this system to demonstrate that the decrease in the p300GBD-GRIP1 interaction is not a non-specific effect.

Figure 13

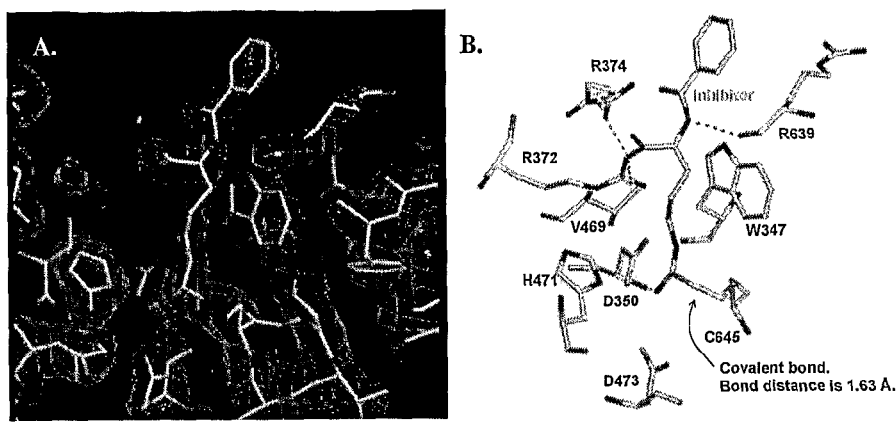

Figure 13. Structure of the PAD4–F3-amidine•calcium complex. *A.* 2 $Fo$ - $Fc$ (blue) and $Fo$ - $Fc$ (red) electron density map of the active site, contour level s=1.0 and 3.0, respectively. PAD4 and F3-amidine are shown in stick format, colored yellow and white, respectively. The green dotted line indicates the electron density for the covalent bond formed between Cys645 and F3-amidine. *B.* Active site structure of the PAD4–F3-amidine•calcium. F3-amidine and PAD4 are shown in stick format (colored orange and white, respectively). Red dotted lines indicate potential hydrogen bonds.

Figure 14. Structural comparison of the PAD4•$Ca^{2+}$•F3-amidine and the PAD4•$Ca^{2+}$•BAA complexes.

Figure 15. Plots of product formation versus time in presence of 25 mM of H2-amidine, H3-amidine and H4-amidine.

Figure 16. Rapid dilution of a preformed complex of PAD4•F2-amidine, PAD4•F4-amidine, PAD4•Cl2-amidine, or PAD4•Cl4-amidine into assay buffer containing excess substrate.

Figure 17. H3-amidine is a competitive inhibitor of PAD4. The Lineweaver-Burk plots (1/vi versus 1/[BAEE]) depicted above are consistent with H3-amidine being a competitive inhibitor. For these studies, the steady state kinetic parameters for the deimination of BAEE were determined in the absence and presence of increasing amounts of H3-amidine.

Figure 18

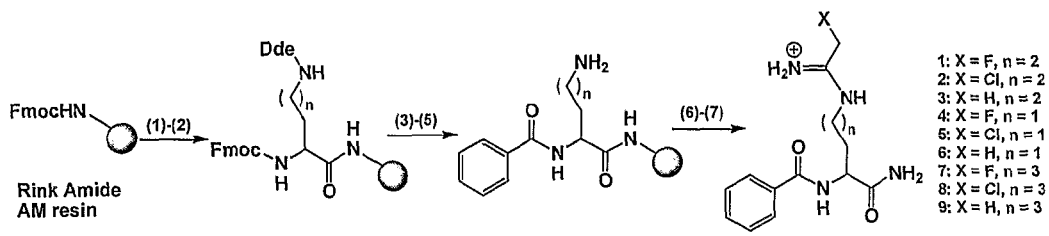

Figure 18: Solid-phase synthesis of haloacetamidine-based PAD4 inactivators/inhibitors. (1) 20 % piperidine in DMF; (2) Fmoc-AA(Dde)-OH, HOBt, HBTU, NMM, DMF; (3) 20 % piperidine, DMF; (4) benzoyl chloride, NMM, DMF; (5) 2 % hydrazine, DMF; (6) XCH$_2$C(=NH)OEt•HCl, Et$_3$N, DMF; (7) 95 % TFA, 2.5 % TIS, 2.5 % H$_2$O. (X= F, Cl, or H; n=1, AA=Dab; n=2, AA=Orn; n=3, AA=Lys; NMM: N-methyl morpholine; DMF: N, N-dimethylformamide; TFA: trifluoroacetic acid; TIS: triisopropylsilane).

Figure 19. Structures of inactivators and proposed mechanism of inactivation. (A) Structures of BAA, a PAD4 substrate, and the PAD4 inactivators F- and Cl-amidine. (B) Proposed mechanisms of inactivation. (C) Fluorescently labeled PAD4 inactivators.

Figure 20. Representative IC50 data for (4) determined with and without preincubation with calcium.

Figure 21. In vitro labeling of PAD4 with RFA and RCA. The ratio of inactivator to protein is indicated at the top of the gel (*top*). The coomassie stained gels are shown to confirm equal loading of PAD4 in each lane. The numbers refer to the ratio [RXA]/[PAD4].

Figure 23

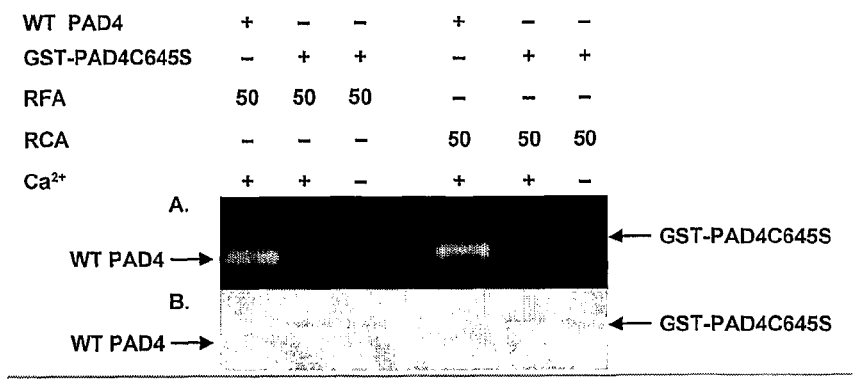

Figure 23. In vitro labeling of wild type PAD4 and the C645S mutant. The GST-PAD4C645S mutant was incubated with either RFA or RCA in the absence or presence of calcium for 1 h. Wild type enzyme lacking the N-terminal GST tag was treated identically. Proteins were separated on a 12% SDS-PAGE gel, fluorescent proteins visualized (A) and then the gels stained in coomassie (B) to confirm that the amount of protein loaded was approximately equal.

Scheme S1. Synthesis of RFA (3) and RCA (4). (a) NHS, EDC, dry $CH_2Cl_2$, r.t., overnight; (b) Anhydrous MeOH, $Et_3N$, 3h; (c) 4 N HCl in 1.4-dioxane, 5h; (d) $Et_3N$, DMF, r.t., overnight; (e) $CuSO_4$, TCEP, ligand, 37°C, 2h.

SYNTHESIS AND USE OF NOVEL INHIBITORS AND INACTIVATORS OF PROTEIN ARGININE DEIMINASES

CROSS REFERENCE TO RELATED APPLICATION

The present application is based on and claims priority to U.S. Provisional Application Ser. No. 60/734,339 having a filing date of Nov. 7, 2005, U.S. Provisional Application Ser. No. 60/791,259 having a filing date of Apr. 12, 2006, and U.S. Provisional Application Ser. No. 60/818,561 having a filing date of Jul. 5, 2006.

BACKGROUND

Protein Arginine Deiminases, are present in humans and a variety of other organisms and consist of a group of isozymes (PADs 1, 2, 3, 4, and 6) that catalyze the $Ca^{2+}$-dependent conversion of arginine to citrulline in a variety of proteins (e.g., histones H2A, H3, and H4).

Protein Arginine Deiminase 4 (PAD4) is a 663 amino acid, 74 kDa, human protein whose deiminating activity (Arg→Cit) appears to be dysregulated in rheumatoid arthritis (RA). Although speculative, it has been suggested that an elevated PAD4 activity causes an overproduction of deiminated proteins that initially leads to a break in self tolerance, and eventually causes the immune system to attack its own tissues. As such, PAD4 represents a novel therapeutic target for RA and inhibition of PAD4 can reduce the levels of deiminated proteins and consequently suppress the immune response directed towards these antigens.

A similar role for PAD2 is thought to play a role in the onset and progression of multiple sclerosis (MS).

Additionally, Protein Arginine Deiminases are thought to play a regulatory role in a number of human cell signaling pathways, including differentiation, apoptosis, and gene transcription.

As such, a need exists for development of PAD-targeted therapeutics, including synthesis methods for novel PAD inhibitors and inactivators. In addition, a need exists for methods of using such inhibitors and inactivators.

SUMMARY

The present disclosure recognizes and addresses the foregoing needs as well as others. Objects and advantages of the disclosure will be set forth in part in the following description, or may be obvious from the description, or may be learned through the practice of the disclosure. In one embodiment of the present disclosure, an inactivator of protein arginine deiminase 4 is disclosed. The inactivator includes:

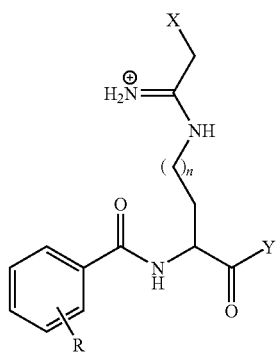

and x includes F, Cl, and H, y includes OH and $NH_2$, R includes H, an allyl group, an alkenyl group, an alknyl group, and n is greater than 0.

In certain embodiments of the present disclosure, x may include F. In some embodiments, x may include Cl. In certain embodiments, the concentration of inactivator that yields half-maximal activity of protein arginine deiminase 4 may be less than about 50 μM. In certain embodiments, the concentration of inactivator that yields half-maximal activity of protein arginine deiminase 4 may be less than about 25 μM. In certain embodiments, the concentration of inactivator that yields half-maximal activity of protein arginine deiminase 4 may be less than about 10 μM.

In yet another exemplary embodiment of the present disclosure, an inactivator of protein arginine deiminase 4 is described. The inactivator includes

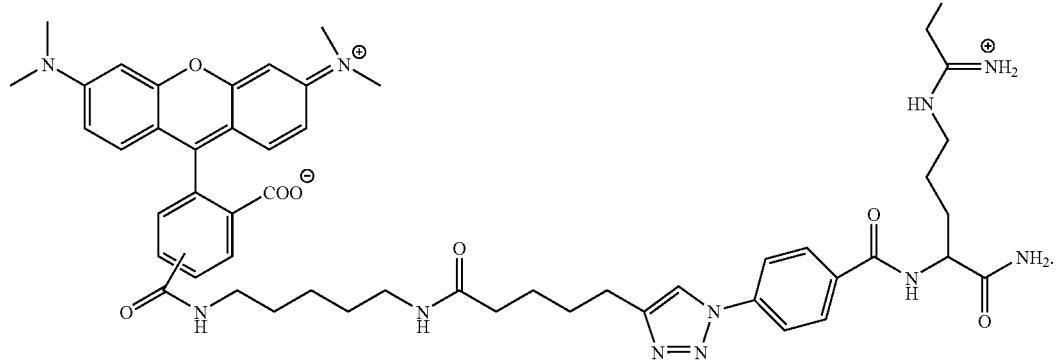

and x includes F and Cl.

In still other exemplary embodiments of the present disclosure, methods of inactivating protein arginine deiminase 4 are disclosed. Such methods include contacting protein arginine deiminase 4 with the inactivators described herein.

In still another embodiment of the present disclosure, a method for synthesis of a protein arginine deiminase 4 inactivator is described. The method includes on-resin coupling of an acetimidate to an ornithine to form a compound, and cleaving of the compound from the resin.

Other features and aspects of the present disclosure are discussed in greater detail below.

DESCRIPTION OF THE DRAWINGS

A full and enabling disclosure, including the best mode thereof to one of ordinary skill in the art, is set forth more particularly in the remainder of the specification, including reference to the accompanying figures in which:

FIG. 2 illustrates potential mechanisms of PAD inactivation;

FIG. 5 illustrates time course of inhibition results;

FIG. 7 illustrates rapid dilution time course results;

FIG. 9 illustrates structures of (halo)acetamidine-based PAD4 inhibitors/inactivators and potential mechanisms of inactivation;

FIG. 10 illustrates calcium and substrate dependence of Cl3-amidine induced inactivation;

FIG. 11 illustrates that Cl3-amidine is an irreversible time and concentration dependent inactivator of PAD4;

FIG. 12 illustrates that Cl3-amidine inhibits the PAD4 mediated enhancement of the p300 GBD-GRIP1 interaction in CV-1 cells;

FIG. 13 illustrates the structure of the PAD4-F3-amidine.calcium complex;

FIG. 18 illustrates solid-phase synthesis of haloacetamidine-based PAD4 inactivators/inhibitors;

FIG. 23 illustrates in vitro labeling of wild type PAD4 and the C645S mutant.

DETAILED DESCRIPTION

It is to be understood by one of ordinary skill in the art that the present discussion is a description of exemplary embodiments only, and is not intended as limiting the broader aspects of the present disclosure, which broader aspects are embodied in the exemplary construction.

The present disclosure is generally directed to inhibitors and inactivators of protein arginine deiminases (PAD). The PAD inhibitors and inactivators described herein are a group of acetamidine-based organic molecules that possess demonstrable inhibitory potency in the μM range to target multiple PAD isozymes.

Figure 1:
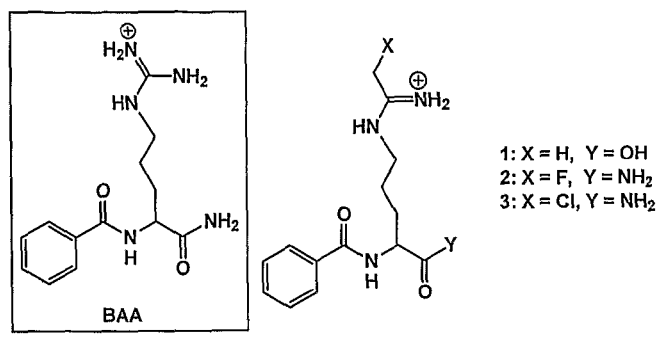
FIG. 1 illustrates structures of (halo)acetamidine-based PAD4 inhibitors and inactivators.

Referring to FIG. 1, basic structures of (halo)acetamidine (HA) based inhibitors and inactivators synthesized in accordance with one embodiment of the present disclosure are illustrated. Such structures can be designed to mimic the structure of small molecule PAD substrates, such as benzoylated arginines. From a structural perspective, the (halo)acetamidine compounds can be useful because they are positively charged, they closely mimic the structure of arginine, and they possess potential H-bond donors for both Asp350 and Asp473 (Protein Arginine Deiminase 4), two active site residues that are important for substrate recognition and catalysis.

Referring to FIG. 2, halide containing (halo)acetamidine compounds of the present disclosure inactivate PAD isozymes by using one of two likely mechanisms, as illustrated. The proposed mechanisms are based on the structural similarities between the compounds described in the present disclosure and halomethyl ketones, which are known to inactivate Cys proteases.

Figure 3:
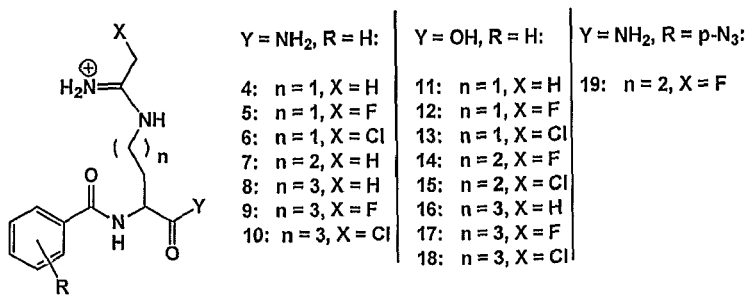
FIG. 3 illustrates structures of other (halo)acetamidine-based PAD4 inhibitors/inactivators.

The (halo)acetamidine compounds described in accordance with the present disclosure are attractive inhibitors and/or inactivators because they are unlikely to target other arginine modifying enzymes, such as Nitric Oxide Synthase (due to the fact that the compounds lack free α-amino and α-carboxyl groups). Referring to FIG. 3, numerous (halo)acetamidine inhibitors and/or inactivators can be formed in accordance with the present disclosure.

For instance, in one embodiment of the present disclosure, a PAD inhibitor/inactivator can have the following structure:

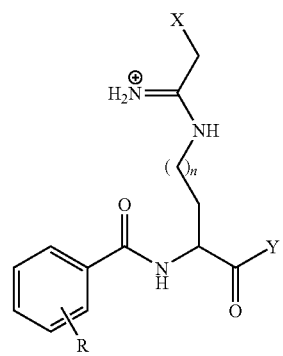

In some embodiments, such a structure can inactivate Protein Arginine Deiminase 4 (PAD4). In some embodiments, x includes F, Cl, H. Additionally, y includes OH and $NH_2$, R includes H, an alkyl group, an alkenyl group, and an alknyl group, and n is greater than 0.

Figure 19:
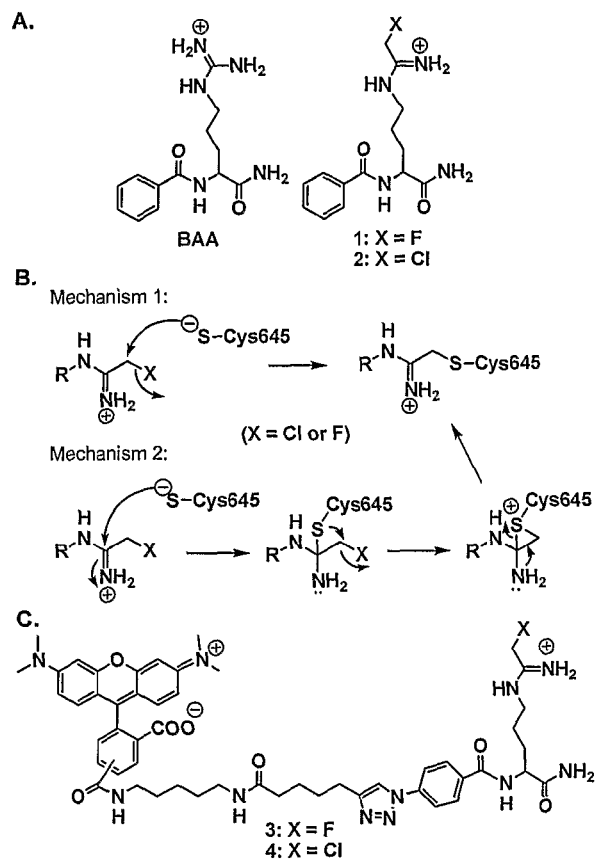
FIG. 19 illustrates structures of inactivators and proposed mechanism of inactivation.
Figure 24:
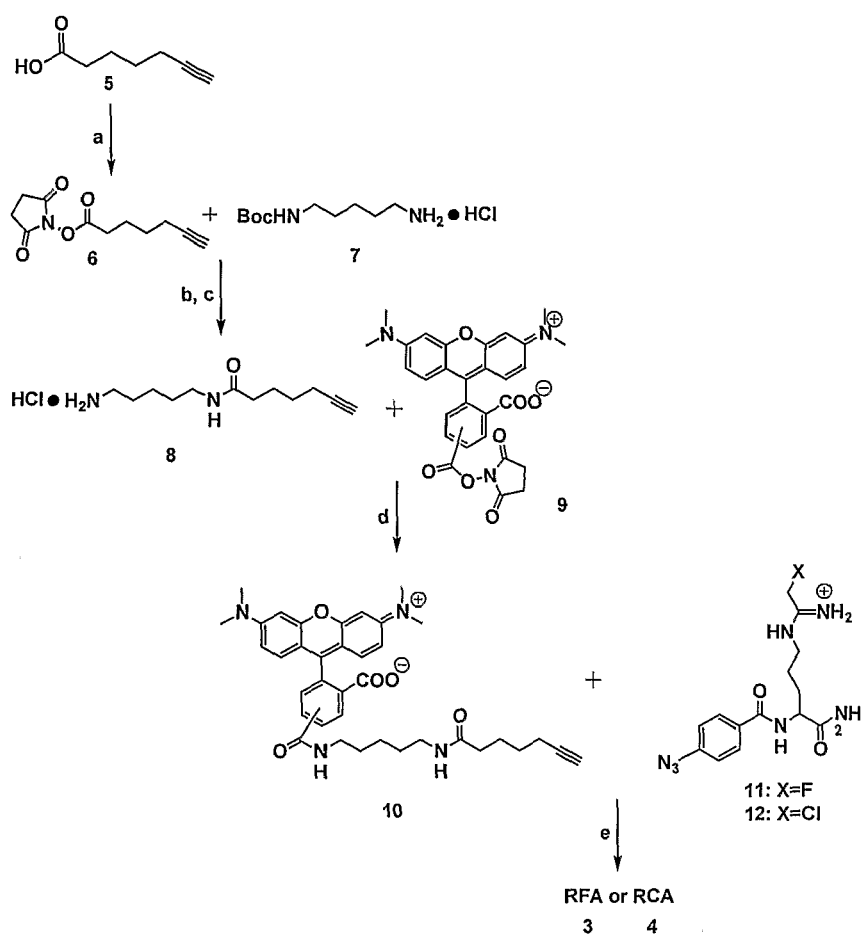
FIG. 24 illustrates synthesis of RFA and RCA.

In some embodiments, fluorescently tagged PAD4 inactivators, rhodamine-tagged F-amidine (RFA) and rhodamine-tagged Cl-amidine (RCA) can be synthesized. Such compounds preferentially label the active, i.e. calcium bound, form of the enzyme. In this regard, referring to FIG. 19, in some embodiments of the present disclosure, a PAD inhibitor/inactivator can have the following structure:

methodology that involves the on-resin coupling of an ethyl haloacetimidate hydrochloride to N-α-4-azidobenzoyl ornithine (Scheme S1—FIG. 24). Subsequently, such a compound is cleaved from the resin and can be coupled to a previously described rhodamine-alkyne construct via the copper(I)-catalyzed azide-alkyne [3+2]cycloaddition reaction and then purified by reverse phase HPLC.

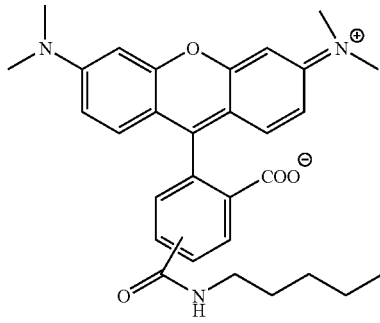
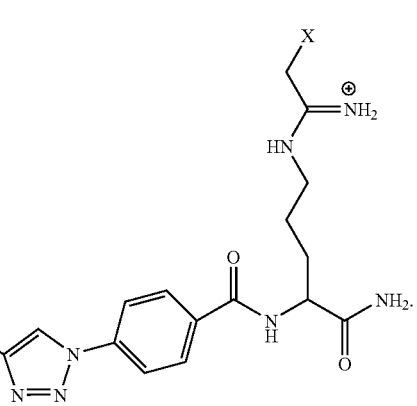

In some embodiments, such a structure can inactivate Protein Arginine Deiminase 4 (PAD4). In some embodiments, x includes F, Cl, and H.

Referring again to FIG. 3, compounds 15 and 19 are also inhibitors and/or inactivators of PAD4 with half-maximal activity values ($IC_{50}$) in the low micromolar range. The $IC_{50}$s of compounds 15 and 19 are 6.67±0.33 (μM) and 25.54±5.57 (μM), respectively.

In some embodiments, the concentration of compounds of the present disclosure that yield half-maximal activity of PAD4 is less than about 50 μM. In certain embodiments, the concentration of compounds of the present disclosure that yield half-maximal activity of protein PAD 4 is less than about 25 μM. In some embodiments, the concentration of compounds of the present disclosure that yield half-maximal activity of PAD4 is less than about 10 μM.

Other molecules described herein can be readily synthesized using the methodologies described in the present disclosure.

For instance, in some embodiments, compounds of the present disclosure can be synthesized by benzoylating commercially available L-$N^5$-(1-iminoethyl)-ornithine dihydrochloride; whereas in other embodiments, the synthesis of compounds can utilize a solid phase synthetic methodology that involves the on-resin coupling of an ethyl-(halo)acetimidate hydrochloride to N-α-benzoyl ornithine. Such reactions can be extended to generate a variety of other acetamidine-containing compounds because acetimidate hydrochlorides can be obtained from commercially available acetonitrile derivatives in a one-step synthesis. Many of the compounds can be obtained in >90% purity after cleavage from the resin and can be further purified by reverse phase HPLC. Some such compounds are quite stable at physiological pH (pH 7.0), as evidenced by the fact that negligible decomposition has been observed even after a 5-day incubation at room temperature.

In some embodiments, a fluorescent tag can be added in a bio-orthogonal manner either before or after the inactivator has undergone reaction with the protein of interest. The synthesis of RFA and RCA, can utilize a solid phase synthetic In some embodiments of the present disclosure, a series of analogs can be synthesized to identify the effects of positioning and leaving group identity on inactivation. In this regard, the correct positioning of the haloacetamidine warhead may be important for both reaction with the enzyme and enhanced potency. In one embodiment, Cl3-amidine can be utilized as a potent and bioavailable inactivator. The structural basis for the inactivation of PAD4 by F3-amidine indicates that such compounds inactivate PAD4 by the specific modification of Cys645, via the formation of a thioether linkage. With appropriate functionalization, such compounds can form the basis for the synthesis of novel activity-based protein profiling reagents that can be useful for isolating the active form of the enzyme from cell lines and tissues; thereby enabling the identification of in vivo post-translational modifications.

In some embodiments, the haloacetamidine-based inactivators of PAD4 are lead compounds for the treatment of RA, in addition to chemical probes that can help to identify and decipher the physiological roles of such enzymes in human cell signaling and how this relates to the onset and progression of RA.

The PAD inhibitors and inactivators described in this disclosure represent a novel therapeutic approach for disease including, for example, rheumatoid arthritis and multiple sclerosis. In addition, the inhibitors and inactivators described in this disclosure are useful small molecular probes that can be used to discern the roles of individual PAD isozymes in physiological processes. For example, the deiminating activity of PAD4 has been demonstrated to contribute to the regulation of eukaryotic (i.e., human) gene transcription and PAD inhibitors/inactivators can be used to characterize the contribution of PAD enzyme activity to the complex processes that control gene transcription in humans.

Such compounds can also often overcome the limitations of common methods used to study specific processes in vivo (e.g. knockout mice, RNAi). For example, small molecule inhibitors are readily added to culture media at specific time points and thereby limit secondary effects caused by the continuous absence of the target, as occurs in knockout mice. Because PAD knockout mice have not been described, the development of PAD-selective inhibitors may be welcomed by the biological community studying PAD function. And while RNA; can be used for the short term ablation of protein expression, and thereby enzymatic activity, this methodology cannot distinguish between effects caused by the loss of enzymatic activity and the loss of the protein itself, which can occur if the protein itself is required for the formation of a higher order complex. Additionally, it is not clear whether RNA; can ablate PAD4 activity in all cell types because PAD4 protein is present in macrophages despite the fact that its mRNA is undetectable.

The following examples are provided to illustrate the present disclosure and are not intended to limit the scope of the invention.

EXAMPLES

Example 1

Figure 4:
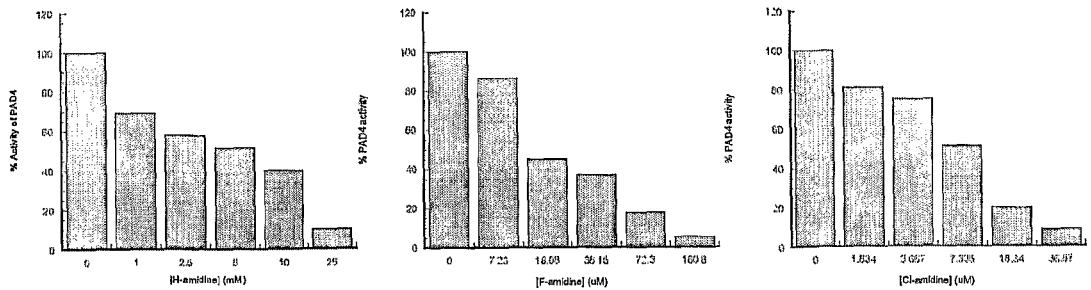
FIG. 4 illustrates PAD4 activity data obtained by $IC_{50}$ assays.

To evaluate the inhibitor potency of the (halo)amidines (HA) described herein, the concentration of an inhibitor that yields half maximal PAD4 activity ($IC_{50}$) was determined for compounds 1, 2, and 3. FIG. 4 graphically depicts the dependence of PAD4 activity on inhibitor concentration and the $IC_{50}$s for compounds 1, 2 and 3 are tabulated in Table 1. $IC_{50}$s can be determined by nonlinear curve fitting of the concentration-activity data to Equation 1 indicated below. These $IC_{50}$ values provide a preliminary evaluation of the relative potency of all three compounds with respect to PAD4. For example, preliminary evaluation shows that compound 3 is approximately 3 times more potent than compound 2 and approximately 600 times more potent than compound 1.

Figure 6:
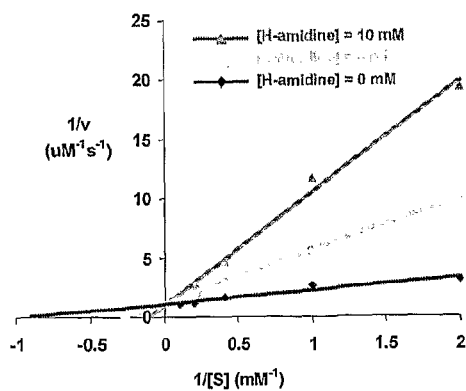
FIG. 6 illustrates Lineweaver-Burk transformation of substrate concentration-rate data.
Figure 8:
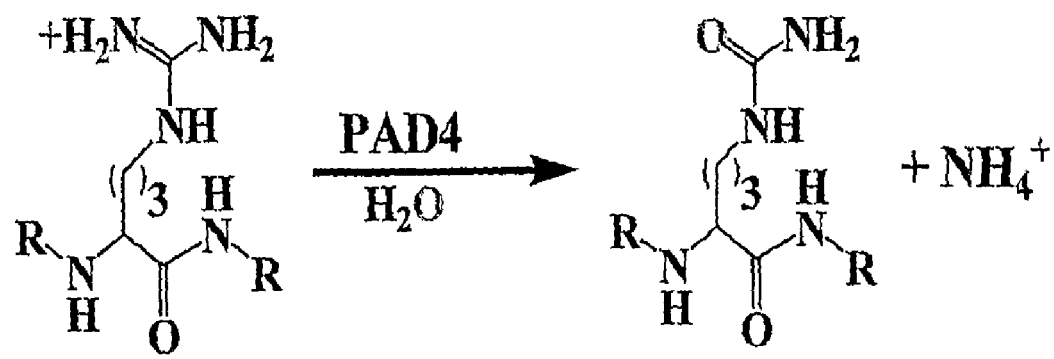
FIG. 8 illustrates Protein Arginine Deiminase 4 deiminating activity.

The HAs described herein, including the H-Amidine, can be covalent inactivators of PAD4. To test this possibility, time courses of product formation was monitored in either the absence or presence of H-, F-, or Cl-Amidine. The results of these preliminary experiments are depicted in FIG. 5 and indicate that H-Amidine does not display time dependent inhibitory properties—indicating that this compound is a reversible inhibitor. The inhibitory properties of compound 1 have been characterized further and the results indicate that this compound is a linear competitive inhibitor of PAD4 (FIG. 6; $K_{is}$=1.7±0.2 mM).

In contrast, compounds 2 and 3 have displayed in preliminary experiments time dependent inhibition properties (FIG. 5), i.e., the progress curves for compounds 2 and 3 are non-linear and reach a plateau value (steady state rate $v_s$=0) given enough time. On the basis of the preliminary results, rapid dilution time course experiments were performed (FIG. 7) to differentiate between reversible and irreversible inhibition. The results of these experiments indicate that there may be no recovery of activity upon dilution of pre-formed PAD4.Inactivator complexes into assay buffer containing only substrate; thereby indicating that these compounds are irreversible inactivators of PAD4.

The present invention introduces a group of acetamidine-based organic PAD inhibitors/inactivators that have been successfully synthesized. Compound 1 is a reversible linear competitive inhibitor of PAD4 ($K_{is}$=1.7±0.2 mM); whereas compounds 2 and 3 are irreversible inactivators of PAD4 with $IC_{50}$ values in the low μM range. These molecules are novel potent PAD4 inhibitors and/or inactivators. Optimization based on these molecules will give rise to more potent and selective PAD4 inhibitors/inactivators that can ultimately be used as treatments for RA and MS.

PAD4 used in this work was GST-cleaved full-length PAD4 that was purified. A recombinant human PAD4 *Escherichia coli* expression system that was obtained from the Yamada group was transformed into *E. coli* Rosetta cells (EMD Biosciences) for the expression of fall-length PAD4 with an 8-residue N-terminal linker that is fused in frame to a PreScission protease cleavable GST tag. The predicted molecular mass of PAD4 including this 8-residue linker is 74879 g/mol.

General procedure for the synthesis of N-α-benzoyl-$N^5$-(1-iminoethyl)-L-ornithine hydrochloride—compound 1 (Scheme 1)

A solution of benzoyl chloride (34 mg, 0.03 ml, 0.245 mmol) in 6 ml $CH_2Cl_2$ was added to a solution of L-$N^5$-(1-iminoethyl)-ornithine dihydrochloride in 15 ml $ddH_2O$ containing sodium bicarbonate (695 mg, 8.3 mmol). This reaction mixture was stirred vigorously at room temperature (r.t.) for 6 hours. After $CH_2Cl_2$ was removed from the reaction mixture, 6M HCl was added dropwise to the reaction mixture until no gas bubbles were produced. From this neutralized reaction mixture compound 1 was separated by preparative HPLC and appeared as white powder upon freeze-drying.

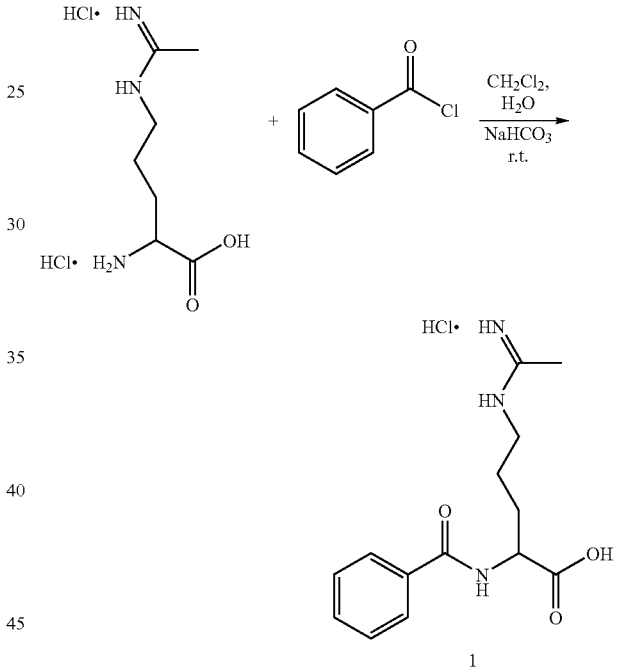

General Procedure for the Synthesis of Rink Amide AM Resin-Bound N-α-benzoyl Ornithine—Compound 20 (Scheme 2)

The solid phase synthesis of compounds 2 and 3 utilizes a common resin bound intermediate—compound 20. The synthesis of this intermediate is described below.

Step A—Removal of Fmoc Group from Resin

Rink Amide AM Resin (300 mg, 0.186 mmol, 1 eqiv.) was pre-swelled in ~5 ml DMF for 1 hour. The DMF was then filtered away and the resin was washed twice with DMF. 5 ml of 20% piperidine (in DMF) was added to the resin and the suspension was rocked gently at r.t. for 20 min. This treatment was repeated once. The resin beads were washed three times with DMF (5 ml each time).

Step B—Coupling of Protected Ornithine to Resin

Fmoc-Orn(Dde)-OH (386 mg, 0.744 mmol, 4 equiv.), HOBt (114 mg, 0.744 mmol, 4 equiv.) and HBTU (282 mg, 0.744 mmol, 4 equiv.) were dissolved in 2.3 ml DMF. This mixture was let stand at room temperature for 10 min before 0.4 M N-methylmorpholine (in DMF) (3.7 ml, 1.488 mmol, 8 equiv.) was added to it. The resin was treated with this new mixture with gentle rocking for ~3 h. After the solution was filtered away, the resin was washed three times with DMF (5 ml each time).

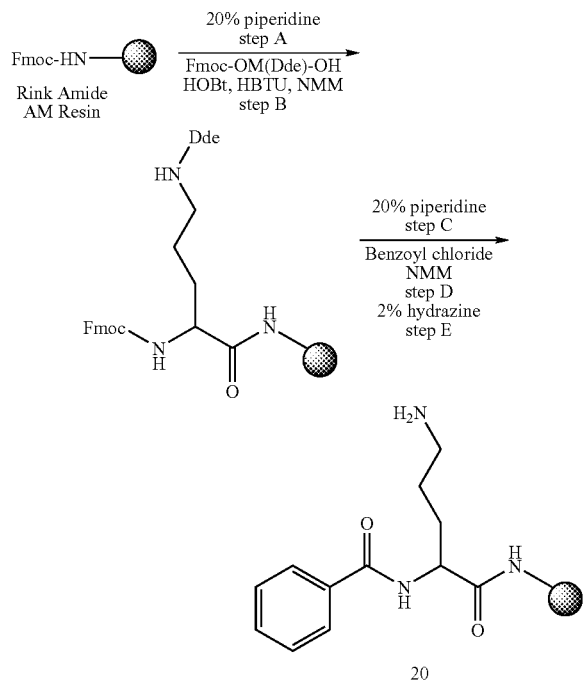

— the resin-bound intermediate used to synthesize compounds 2 and 3. (A) Removal of Fmoc group from resin; (B) coupling of protected ornithine to resin; (C) removal of FMOC group from resin-bound ornithine; (D) coupling of benzoyl group to α-NH₂ of ornithine; (E) removal of Dde group from ornithine Step C—Removal of Fmoc Group from Protected Ornithine 5 ml of 20% piperidine (in DMF) was added to the resin and the suspension was rocked gently at room temperature for 20 minutes. This treatment was repeated once. The resin was then washed three times with DMF (5 ml each time).

Step D—Coupling of Benzoyl Group to α-NH₂ of Ornithine

A mixture of benzoyl chloride (105 mg, 0.09 ml, 0.744 mmol, 4 equiv.) and 0.4 M N-methylmorpholine (in DMF) (1.488 mmol, 8 equiv.) was added to the resin. The suspension was rocked gently at room temperature overnight (about 16 hours). After the solution was filtered away, the resin was washed three times with DMF (5 ml each time).

Step E—Removal of Dde Group from Protected Ornithine

The resin was treated with 5 ml of 2% hydrazine (in DMF) for about 2 hours and then washed three times with DMF (5 ml each time), two times with ethanol and two times with methylene chloride. After being dried under vacuum overnight, the resin was used in the next reaction step.

General Procedure for the Synthesis of Ethyl Haloacetimidate Hydrochloride—Compounds 21 and 22 (Scheme 3)

Step F

Fluoro(or chloro)acetonitrile (3.4 mmol), HCl (1.0 M solution in diethyl ether) (3 ml, 3 mmol) and absolute ethanol (0.2 ml, 3.4 mmol) were added sequentially to a 5-ml round-bottomed flask at room temperature. This reaction mixture was stirred at room temperature overnight (about 18 hours). A white precipitate appeared during the reaction process. This precipitate was filtered, washed with cold ether, dried under vacuum and then directly used in step G without further purification.

General procedure for the synthesis of N-α-benzoyl-N⁵-(2-halo-1-iminoethyl)-L-ornithine amide—compounds 2 and 3 (Scheme 3)

Step G

Ethyl fluoro(or chloro)acetimidate hydrochloride (17 mg, 0.124 mmol), dry triethyl amine (13 mg, 0.124 mmol) and Rink Amide AM resin-bound N-α-benzoyl-ornithine (50 mg, 0.027 mmol) were mixed in 1 ml dry DMF. This reaction mixture was stirred at room temperature overnight (about 16 hours) under nitrogen. Then the resin was filtered and washed sequentially with DMF, ethanol and methylene chloride.

Step H

The resin was incubated with a mixture of TFA/TIS/H₂O (95%/2.5%/2.5%) for 3 hours with gentle rocking before it was filtered and washed with 95% TFA (in ddH₂O) several times. The filtrate and all the washings were combined. From the combined solution, TFA was blown off with flowing nitrogen. To the remaining residue, cold ether was added to yield a white precipitate. This precipitate was washed twice with cold ether and then freeze-dried. Purification with preparative HPLC yielded N-α-benzoyl-N⁵-(2-fluoro(or chloro)-1-iminoethyl)-L-ornithine amide (compounds 2 and 3) as white hydroscopic powders upon freeze-drying.

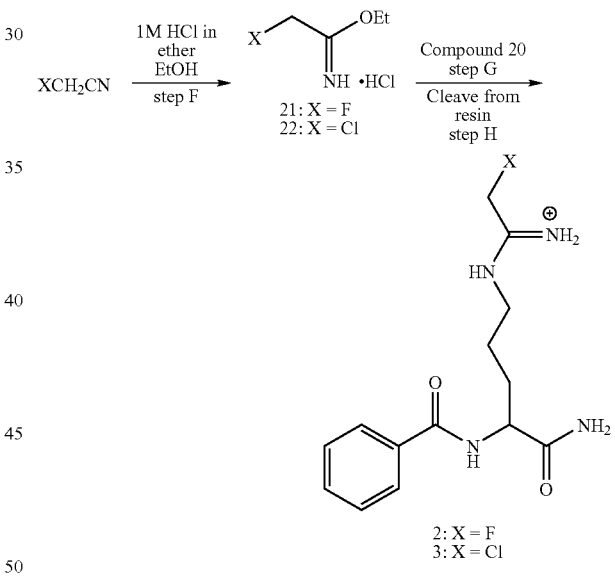

Identification of Compounds 1, 2 and 3

N-α-benzoyl-N⁵-(1-iminoethyl)-L-ornithine (compound 1). ¹HNMR (400 MHz, CD₃OD) δ (ppm): 7.90-7.49 (m, 5H), 4.71-4.68 (dd, 1H), 3.37-3.32 (m, 2H), 2.23 (d, 3H), 2.14-1.82 (m, 4H). ¹³CNMR (400 MHz, CD₃OD) δ (ppm): 174.96, 170.51, 166.19, 135.16, 133.00, 129.61, 128.49, 53.46, 43.00, 29.82, 25.31, 18.86. MS-ES⁺: 278. HRMS ($C_{14}H_{20}N_3O_3^+$): calculated 278.1505, observed 278.1497. Lyophilization of Compound 1, after reverse phase HPLC purification, results in the formation of the TFA salt. Yield 68.1%.

N-α-benzoyl-N⁵-(2-fluoro-1-iminoethyl)-L-ornithine amide (compound 2). ¹HNMR (400 MHz, CD₃OD) δ (ppm): 7.90-7.46 (m, 5H), 5.30-5.19 (d, $^2J_{H-F}$=45.3 Hz, 2H), 4.65-4.61 (dd, 1H), 3.47-3.36 (m, 2H), 2.03-1.73 (m, 4H). ¹³CNMR (400 MHz, CD₃OD) δ (ppm): 176.46, 170.32, 164.44-164.25 ($^2J_{C-F}$=20 Hz), 135.02, 133.10, 129.64, 128.52, 79.85-78.07 ($^1J_{C-F}$=179 Hz), 54.13, 42.98, 30.37, 25.11. $^{19}$FNMR (400 MHz, CD$_3$OD) δ (ppm): −158.03, −158.15, −158.27 ($^2J_{H-F}$=45.2 Hz). MS-ES$^+$: 295. HRMS (C$_{14}$H$_{20}$FN$_4$O$_2^+$): calculated 295.1570, observed 295.1569. Elemental analysis (C$_{16}$H$_{20}$F$_4$N$_4$O$_4$): calculated C, 47.06%; H, 4.94%. found C, 44.72%; H, 4.86%. Lyophilization of Compound 2, after reverse phase HPLC purification, results in the formation of the TFA salt. Yield 36.6%.

N-α-benzoyl-N$^5$-(2-chloro-1-iminoethyl)-L-ornithine amide (compound 3). $^1$HNMR (400 MHz, CD$_3$OD) δ (ppm): 7.79-7.37 (m, 5H), 4.56-4.52 (dd, 1H), 4.26 (s, 2H), 3.34-3.20 (m, 2H), 1.98-1.64 (m, 4H). $^{13}$CNMR (400 MHz, CD$_3$OD) δ (ppm): 176.46, 170.31, 164.68, 135.03, 133.08, 129.63, 128.53, 54.17, 43.53, 40.11, 30.37, 25.00. MS-ES$^+$: 311. HRMS (C$_{14}$H$_{20}$ClN$_4$O$_2^+$): calculated 311.1275, observed 311.1266. Elemental analysis (C$_{16}$H$_{20}$ClF$_3$N$_4$O$_4$): calculated C, 45.24%; H, 4.75%; F, 13.42%. found C, 43.04%; H, 4.67%, F, 13.50%. Lyophilization of Compound 3, after reverse phase HPLC purification, results in the formation of the TFA salt. Yield 71.4%.

Inhibition/Inactivation Studies:

IC$_{50}$ Assays

IC$_{50}$ values of compounds 1, 2, and 3 were determined with variable concentrations of these compounds in a reaction buffer containing 100 mM HEPES (pH 7.6), 50 mM NaCl, 250 mM TCEP, and 10 mM CaCl$_2$. The aforementioned reaction mixtures were pre-incubated with PAD4 (0.5 µM) at 37° C. for 10 minutes prior to the addition of BAEE (1 mM final concentration) to initiate the reaction. After 20 minutes the reactions were quenched by flash freezing in liquid nitrogen. For color development, 200 µL of freshly prepared COLDER solution (2.25 M H$_3$PO$_4$, 4.5 M H$_2$SO$_4$, 1.5 mM NH$_4$Fe (SO$_4$), 20 mM diacetyl monoxime, and 1.5 mM thiosemicarbazide) was added to each of the quenched reactions, vortexed to ensure complete mixing, and then incubated at 95° C. for 30 minutes. The absorbance at 540 µm was then measured and compared to a Cit standard curve to determine the concentration of Cit produced during the course of the reactions. IC$_{50}$ values were determined by fitting the concentration-response data to Equation 1 using the Kaleidagraph™ version 3.09 software package, where [I] refers to the concentration of inhibitors.

$$\text{Fractional activity of PAD4} = 1/(1+([I]/IC_{50})) \quad \text{(Eq. 1)}$$

The concentration of an inhibitor that corresponds to the midpoint (fractional activity=0.5) was referred to as the IC$_{50}$.

Rapid Dilution Time Course Inhibition Assays

In order to determine the reversibility of inhibition, rapid dilution time course experiments were performed for compounds 2 and 3 by measuring the recovery of PAD4 activity over time after a rapid 95-fold dilution of a PAD4-inhibitor complex. PAD4-inhibitor complexes were pre-formed by incubating PAD4 (9.5 µM) with inhibitor (167 µM) at 37° C. for 30 min. The reaction was initiated by the addition of 6.3 µL of the preformed PAD4-inhibitor complex to a reaction buffer containing 10 mM BAEE, 100 mM HEPES (pH 7.6), 50 mM NaCl, 500 mM TCEP and 10 mM CaCl$_2$ (final volume 600 µL). At various time points (0, 2, 4, 6, 10, 15 min), 60 µl of the reaction was withdrawn and quenched by flash freezing in liquid nitrogen. Color development and absorbance measurement at 540 nm of the samples were done as described for the IC$_{50}$ assays.

Time Course Inhibition Assays

Time course experiments were performed in assay buffers containing 10 mM BAEE, 100 mM HEPES (pH 7.6), 50 mM NaCl, 500 µM TCEP and 10 mM CaCl$_2$ in the presence of various amounts of inhibitors. The assay buffers were pre-incubated at 37° C. for 10 minutes. Reactions were initiated by addition of PAD4 to a final concentration of 0.25 µM. At different time points, 60 µl of the reactions was withdrawn and quenched by flash freezing in liquid nitrogen. Color development and absorbance measurement at 540 nm of the samples were done as described in IC$_{50}$ assays. The data obtained for compound 1 were fit to a simple linear equation; whereas the data obtained for compounds 2 and 3 were fit to Equation 2 using the Kaleidagraph™ version 3.09 software package.

$$[P] = v_{i[}1-\exp(-k_{obs}t)]/k_{obs} \quad \text{(Eq. 2)}$$

where $v_i$ is the initial velocity, $k_{obs}$ is the pseudo-first-order rate constant, and [P] refers to the concentration of citrulline produced during the reaction process.

Inhibition Assays with Compound 1

In order to determine the mode of inhibition of compound 1, the steady state kinetic parameters for BAEE were determined in the absence and presence of various amounts of compound 1 (0, 5, 10 mM). BAEE and compound 1 were pre-incubated in the assay buffer (100 mM HEPES (pH 7.6), 50 mM NaCl, 500 µM TCEP, 10 mM CaCl$_2$) for 10 minutes at 37° C. Reactions were initiated by the addition of PAD4 to a final concentration of 0.2 µM. After incubation at 37° C. for 15 min, the reactions were quenched by flash freezing in liquid nitrogen. Color development and absorbance measurement at 540 nm of the quenched reactions were done as described in IC$_{50}$ assays. The initial rates obtained from the kinetic assays were fit to the Michaelis-Menten equation (Equation 4), using the Kaleidagraph™ version 3.09 software package.

$$v = V_m[S]/(K_m+[S]) \quad \text{(Eq. 4)}$$

Example 2

As a part of ongoing efforts to develop PAD4-targeted therapeutics, we have synthesized and characterized N-α-benzoyl-N$^5$-(2-fluoro-1-iminoethyl)-L-ornithine amide (1, F3-amidine, FIG. 9), a PAD4 inactivator that is significantly more potent than either taxol (IC$_{50}$~5 mM) or 2-chloroacetamidine ($k_{inact}/K_I$=35 M$^{-1}$min$^{-1}$), two known PAD inhibitors. In vitro studies with F3-amidine reveal that it irreversibly inactivates PAD4 in a calcium-dependent manner via the specific modification of Cys645 (vide infra), an active site residue that is important for catalysis—Cys645 acts as a nucleophile to form a thiouronium intermediate that is ultimately hydrolyzed to form Cit. The inhibitory properties of F3-amidine have been evaluated in vivo and the results indicate that this compound is bioavailable. In an effort to identify the effects of warhead positioning and the identity of the leaving group, we synthesized a series of analogs in which the length of the side chain and the identity of the halide were systematically varied. Herein is reported the results of these studies, as well as the identification of a significantly more potent PAD4 inactivator, N-α-benzoyl-N$^5$-(2-chloro-1-iminoethyl)-L-ornithine amide (2, Cl3-amidine, FIG. 9A), that like the parent compound is bioavailable. The structural basis for the inactivation of PAD4 by F3-amidine is also reported.

Results

Design of PAD4 Inactivators/Inhibitors

The initial design of F3-amidine is in part based on its structural homology to N-α-benzoylArg amide (BAA—FIG. 9A), one of the best small molecule PAD4 substrates ($k_{cat}/K_m$: 1.1×10$^4$ M$^{-1}$s$^{-1}$), and can be considered to consist of two major moieties, a fluoroacetamidine-based warhead and a specificity determinant that is expected to target the warhead to the active site of PAD4, where it will react with C645 to form a stable thioether adduct via one of two potential mechanisms (FIG. 9B). To identify PAD4 inhibitors with enhanced potency and to gain insights into the steric and leaving group requirements for PAD4 inactivation, a series of compounds were synthesized in which both the length of the side chain and the leaving group were varied. The lengths of the side chains ranged from 2 to 4 methylene units—thereby allowing us to evaluate the importance of positioning to inactivation—and the fluoro group was replaced with a chloro group. The fluoro group was also replaced with hydrogen to evaluate the requirement for a leaving group. Three potential scenarios were envisioned for H2-, H3-, and H4-amidine (3, 6 and 9 in FIG. 9A), which are detailed here: i) the iminium carbon of the acetamidine moiety would not possess sufficient reactivity with the active site thiolate and the compounds would be competitive inhibitors; ii) the iminium carbon would react with the active site thiolate to form the first tetrahedral intermediate and act as transition state analogs; or iii) the iminium carbon would react with the active site thiolate to form the first tetrahedral intermediate. Subsequently, the intermediate would collapse, resulting in the loss of benzoylated ornithine, and the formation of an irreversible imidothioic acid adduct.

The (halo)acetamidine-based PAD4 inhibitors/inactivators described herein were readily synthesized on the solid phase, analogously to the synthesis of F3-amidine (FIG. 18). Briefly, a Fmoc-protected (main chain) and Dde-protected (side chain) diamino acid, e.g. ornithine, was coupled to Rink Amide AM resin via a standard uronium-based coupling method. Subsequently, the Fmoc was removed with 20% piperidine and the resulting free α-amino group was benzoylated with benzoyl chloride. The side chain amine was then deprotected with 2% hydrazine and reacted with either ethyl fluoro-, ethyl chloro-, or ethyl-acetimidate hydrochloride to form the (halo)acetamidine-based warhead. The acetimidates were readily derived from their corresponding acetonitrile derivatives in a one-step synthesis that involves a reaction between the acetonitrile derivative and ethanol in acidified ether (1M HCl in ether). Final compounds were subsequently cleaved from the resin, purified by reverse phase HPLC, and their structures confirmed by NMR ($^1$H and $^{13}$C) and HR-ESI-MS.

Structure-Activity Relationships

Figure 15:
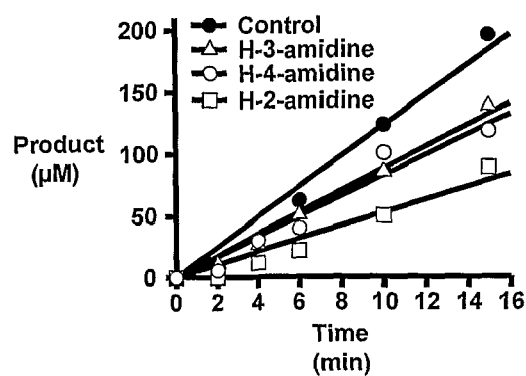
FIG. 15 illustrates plots of product formation versus time in presence of 25 mM of H2-amidine, H3-amidine and H4-amidine.

The inhibitory properties of compounds 2-9 (FIG. 9A) were initially evaluated by determining the concentration of compound that yielded the half maximal activity, i.e. the $IC_{50}$, and comparing the results of these studies to the $IC_{50}$ value obtained for F3-amidine—$IC_{50}$'s were determined under conditions that were identical to those used to determine the $IC_{50}$ for F3-amidine. The results of these initial studies (Table 2) indicate that Cl3-amidine is a significantly more potent inhibitor than F3-amidine—the inhibitory properties of Cl3-amidine are discussed in detail below. Interestingly, H3-amidine, the acetamidine-containing isostere of F3-amidine (and BAA) is a very poor inhibitor of PAD4 ($IC_{50}$>1000 μM). Time course experiments with H3-amidine, and the related H2- and H4-amidine (compounds 6 and 9 (FIG. 9A)), were linear with respect to time (FIG. 15); thereby indicating that on the time scale of these experiments the acetamidine-bearing compounds are reversible PAD4 inhibitors. The reversible nature of the inhibition rules out the possibility that these compounds react with the active site Cys to form the postulated imidothioic acid adduct and the fact that these compounds are such poor inhibitors is inconsistent with their being transition state analogs. The results further suggest that an additional electron-withdrawing group is required to promote reactions between Cys645 and the iminium carbon.

Figure 16:
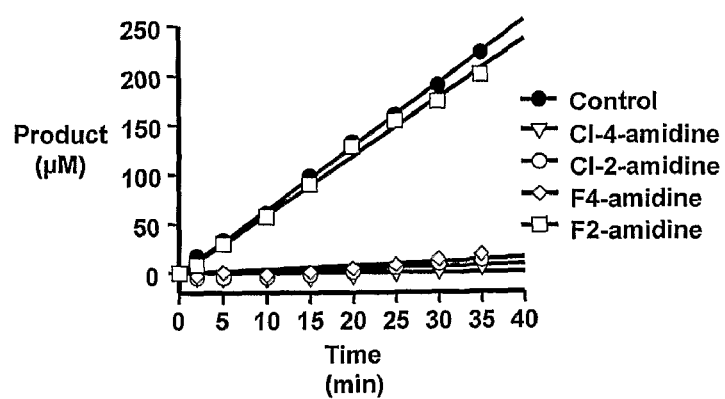
FIG. 16 illustrates rapid dilution of a preformed complex of PAD4.F2-amidine, PAD4.F4-amidine, PAD4.Cl2-amidine, or PAD4.Cl4-amidine into assay buffer containing excess substrate.

Cl2-, F4-, and Cl4-amidine are also relatively poor PAD4 inhibitors with $IC_{50}$'s in the 500 μM range. To determine if Cl2-, F4-, and Cl4-amidine are irreversible inactivators, these compounds were pre-incubated with PAD4 and then rapidly diluted into assay buffer containing an excess of substrate. The results of these experiments (FIG. 16) show no recovery of activity, suggesting that these compounds are, similarly to F3-amidine, irreversible PAD4 inactivators. The fact that compounds with side chains of 2 or 4 methylene units are significantly less potent inhibitors/inactivators than either F3-amidine or Cl3-amidine indicates that the proper positioning of the reactive warhead is critical for reaction with the active site thiolate.

In contrast to the results obtained for Cl2-amidine, its isostere F2-amidine, which contains the fluoro—rather than the chloro-acetamidine warhead, is a significantly less potent PAD4 inhibitor—at 1000 μM F2-amidine, the observed activity was 93% of control. Consistent with its lack of potency is the fact that time courses were linear with respect to time and the rapid dilution time course experiments demonstrated complete recovery of activity (FIG. 16); thereby indicating that this compound is neither a slow binding nor irreversible inactivator of PAD4. The finding that F2-amidine does not irreversibly inactivate PAD4 likely reflects the fact that the side chain of this compound is too short to appropriately position the fluoracetamidine warhead for reaction with Cys645 via Mechanism 2 in FIG. 9B—this compound is unlikely to react via Mechanism 1 due to the intrinsically poor leaving group potential of fluoride. The fact that Cl2-amidine is an irreversible inactivator could either reflect the intrinsic reactivity of the chloro group or alternatively that chloroacetamidines can react with the active site thiolate through either Mechanism 1 or 2 in FIG. 9B; whereas fluoroacetamidines can only react through Mechanism 2.

The importance of a positively charged warhead for inactivator potency was also evaluated by synthesizing the neutral isosteres of F3- and Cl3-amidine, i.e. N-α-benzoyl-N$^5$-(2-fluoroacetyl)ornithine amide, compound 10, and N-α-benzoyl-N$^5$-(2-chloroacetyl)ornithine amide, compound 11. $IC_{50}$'s assays were performed with these compounds; however, no inhibition was noted at even the highest concentration of compound tested, i.e., 500 μM—higher concentrations were not tested because of solubility issues. The simplest explanation for the lack of potency is that they do not form high affinity interactions with the PAD4 active site. This lack of affinity is most likely due to the lack of a positively charged warhead. The presence of hydrogen bond acceptors in the warhead, rather than hydrogen bond donors, as is the case in the acetamidine warhead, could also account for the lack of affinity.

In Vitro Characterization of H3- and Cl3-amidine

The structure-activity relationships described above demonstrate the requirement for an electron-withdrawing group to effect reaction with the active site Cys and further indicate that appropriate positioning of the reactive warhead is important for the inactivation reaction. The detailed inhibitory properties of H3-amidine and Cl3-amidine were also determined (see below) to gain additional insights into both their potency and mechanism of inhibition. Focus was on characterizing these compounds because they are both isosteric with F3-amidine, but Cl3-amidine is significantly more potent, whereas H3-amidine is significantly less potent.

Figure 17:
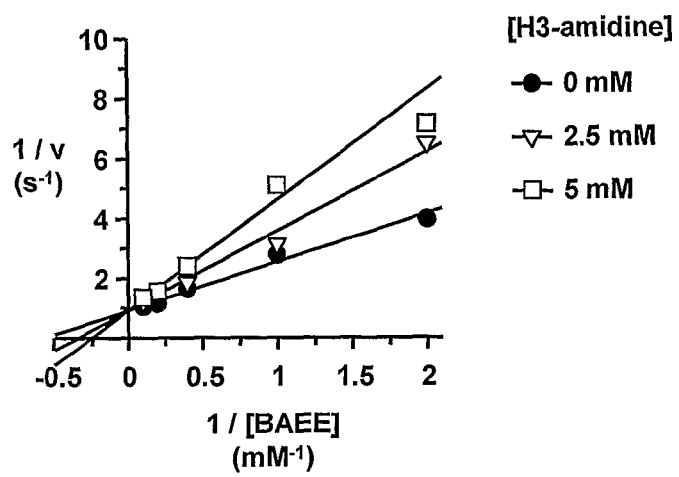
FIG. 17 illustrates Lineweaver-Burk plots (1/vi versus 1/[BAEE]) that are consistent with H3-amidine being a competitive inhibitor.

To further characterize the inhibitory properties of H3-amidine, the steady state kinetic parameters for the deimination of Benzoyl Arg ethyl ester (BAEE) were determined in the absence and presence of increasing amounts of H3-amidine. The results of these studies indicate that H3-amidine is a linear competitive inhibitor of PAD4 (FIG. 17) with a $K_{is}$ in the low mM range ($K_{is}$=3.2±0.9 mM). The reversible nature of the inhibition and the lack of potency clearly demonstrate the significant gains in binding energy that can be achieved through covalent bond formation.

A series of experiments were also performed on Cl3-amidine, which included assays: i) to evaluate the calcium dependence of inactivation; ii) to determine if substrate can protect against inactivation; iii) to confirm the irreversible nature of the enzyme-Cl3-amidine complex; and iv) to more fully characterize the kinetics of inactivation. Initially, the calcium dependence of the $IC_{50}$ was determined. For these studies, Cl3-amidine was pre-incubated with PAD4 in the absence and presence of calcium, prior to the addition of BAEE to initiate the enzyme assay—calcium was also added to the sample pre-incubated in the absence of this metal ion to activate PAD4. These experiments were performed because calcium binding to PAD4 triggers a conformational change that moves His471 and Cys645 into positions that are competent for catalysis; thus, if Cl3-amidine reacts with an active site residue, one would expect it to preferentially inactivate the calcium bound form of the enzyme. The results of these experiments, which are depicted in FIG. 10A, indicate that Cl3-amidine preferentially inactivates the calcium bound form of the enzyme by >10-fold. This result is consistent with previous results reported for F3-amidine and indicates that this compound preferentially inactivates the active form of the enzyme.

To further confirm that Cl3-amidine inactivates PAD4 by the preferential modification of an active site residue, substrate protection experiments were also performed. For these experiments, product formation was monitored as a function of time for two different concentrations of BAEE (2 and 10 mM) in the absence and presence of Cl3-amidine. The results of these experiments (FIG. 10B) clearly establish that the rate of inactivation is significantly higher at the lower concentration of substrate. Thus, substrate can protect against inactivation, consistent with the preferential modification of an active site residue, which based on the precedents obtained for F3-amidine, and the related compound 2-chloroacetamidine, is most likely Cys645.

In order to confirm that Cl3-amidine is an irreversible inactivator of PAD4, rapid dilution time course experiments were performed with this compound. Briefly, pre-formed PAD4-Cl3-amidine complexes were diluted 95-fold into assay buffer containing 10 mM BAEE (7.5×$K_m$) and product formation monitored as a function of time (FIG. 11A). The time courses showed no recovery of PAD4 activity, consistent with the irreversible inactivation of PAD4. Dialysis experiments were also performed on pre-formed PAD4-Cl3-amidine complexes to assay for the recovery of enzymatic activity over a longer time frame; and thereby exclude the possibility that Cl3-amidine is a reversible slow binding inhibitor with a very long half life. Briefly, PAD4 was incubated with Cl3-amidine to affect enzyme inactivation, at which point the enzyme inhibitor complex was dialyzed for about 3.5 h, the buffer exchanged, and then dialyzed for about an additional 16.5 h (20 h total). Activity measurements performed before and after dialysis demonstrated that there was no recovery of activity at either the 3.5 h or 20 h time points, again consistent with the irreversible inactivation of PAD4 (FIG. 11B) and ruling out the possibility that Cl3-amidine is a slow binding inhibitor.

To further define the inhibitory properties of Cl3-amidine, the rate constants for the inactivation process, i.e $K_I$, $k_{inact}$, and $k_{inact}/K_I$, were determined. For these studies, product formation was monitored as a function of time in the absence and presence of different concentrations of Cl3-amidine (FIG. 11C). The non-linear progress curves were fit to Equation 1, $$[Cit]=v_i(1-e^{-k_{obs}t})/k_{obs} \quad (\text{Eq. 1}),$$

where $v_i$ is the initial velocity, $k_{obs}$ is the apparent pseudo-first-order rate constant for inactivation, and [Cit] refers to the concentration of Cit produced during the time course. The pseudo-first-order rate constants were then plotted versus the concentration of Cl3-amidine and the resulting curves fit to Equation 2, $$k_{obs}=k_{inact}[I]/(K_I+[I]) \quad (\text{Eq. 2}),$$

where $k_{inact}$ is the maximal rate of inactivation, $K_I$ is the concentration of inactivator that yields half maximal inactivation, and [I] is the concentration of inactivator. Using this analysis (FIG. 11D) values for $k_{inact}$ and $K_I$ of 2.4±0.2 min$^{-1}$ and 180±33 μM, respectively, were determined. The second order rate constant for Cl3-amidine induced inactivation ($k_{inact}/K_I$=13,000 M$^{-1}$min$^{-1}$) is 4.3-fold higher than that observed for F3-amidine, roughly consistent with its 3.6-fold decrease in the $IC_{50}$ of Cl3-amidine relative to the fluoroacetamidine containing compound. The $k_{inact}/K_I$ obtained for Cl3-amidine is also 370-fold higher than that obtained for 2-chloroacetamidine, i.e. the warhead alone—the $k_{inact}/K_i$ for this compound (35 M$^{-1}$min$^{-1}$) was recently reported by the Fast group. Because the increase in $k_{inact}/K_I$ is mostly driven by a decrease in K, (20 mM for 2-chloroacetamidine versus 180 μM for Cl3-amidine), the improved inactivation kinetics most likely result from the inclusion of the benzoylated ornithine portion in the molecule, which would be expected to provide additional binding energy for the formation of the initial enzyme.Cl3-amidine complex; thereby suggesting that further improvements to potency could be gained by tailoring this portion of the molecule to maximize its interactions with the active site of PAD4.

In Vivo Studies with Cl-3-Amidine

The PAD4 catalyzed deimination of the GRIP1 binding domain of p300 (p300 GBD) is known to enhance interactions between p300 and GRIP1, a nuclear receptor coactivator. Because it has been previously reported that F3-amidine could antagonize this effect in vivo and because Cl3-amidine displays enhanced in vitro potency, its ability to interfere with the PAD4-mediated enhancement of the p300 GBD-GRIP1 interaction was evaluated. For these studies, a previously described mammalian two-hybrid assay was utilized that monitors the efficiency of p300 GBD-GRIP1 interaction as well as the effects of PAD4 on this system (FIG. 12). Briefly, CV-1 cells were transiently transfected with plasmids encoding a luciferase reporter construct, the p300 GBD fused to the Gal4 DNA Binding Domain, the p300 binding domain of GRIP1 (i.e. the AD1 domain) fused to the VP16 Activation Domain (AD), and either wild type PAD4 or the catalytically defective C645S mutant. Cl3-amidine (0-200 μM) was then added to the cell culture medium and the amount of luciferase activity in cell extracts determined. The results clearly indicate that Cl3-amidine antagonizes the PAD4-mediated enhancement of the p300 GBD.GRIP1 interaction in a dose dependent manner and it is noteworthy that Cl3-amidine treatment caused only a minimal reduction in the efficiency of the interaction in Cys645S transfected cells; thereby indicating that the effect of this compound is not a non-specific one. The results obtained for Cl3-amidine not only indicate that it is bioavailable but also reveal that it is significantly more potent than F3-amidine, consistent with its improved in vitro potency.

Structural Basis for Inactivation

To gain further insights into the inactivation properties of F3-amidine, the structure of the wild type PAD4-F3-amidine.calcium complex was determined (FIG. 13). Crystals of the calcium-bound enzyme-inactivator complex were obtained by soaking calcium free crystals in crystallization buffer containing 5 mM $CaCl_2$ and 5 mM of F3-amidine. Diffraction data were then collected and the initial structure derived by molecular replacement using the coordinates of the previously determined PAD4.BAA.calcium complex.

The overall structure of the PAD4-F3-amidine.calcium complex was comparable to the previously determined structure of PAD4 bound to calcium and BAA-PAD4 consists of 3 contiguous domains that include 2 immunoglobulin-like folds that are present in the N-terminal half of the enzyme and a C-terminal catalytic domain. The major difference between these two structures is electron density corresponding to a 1.63 Å covalent bond between Sβ in Cys645 and the Cη atom of F3-amidine (FIG. 13)—the presence of the electron density for this covalent bond was confirmed by analyzing the 2 Fo-Fc and Fo-Fc Fourier maps with contour levels of more than 2σ. In contrast, no electron density for the fluoride atom was apparent in the structure. Note that electron density for F3-amidine was only detected at the active site of the enzyme; thus this compound regiospecifically inactivates PAD4 by modifying Cys645.

Figure 14:
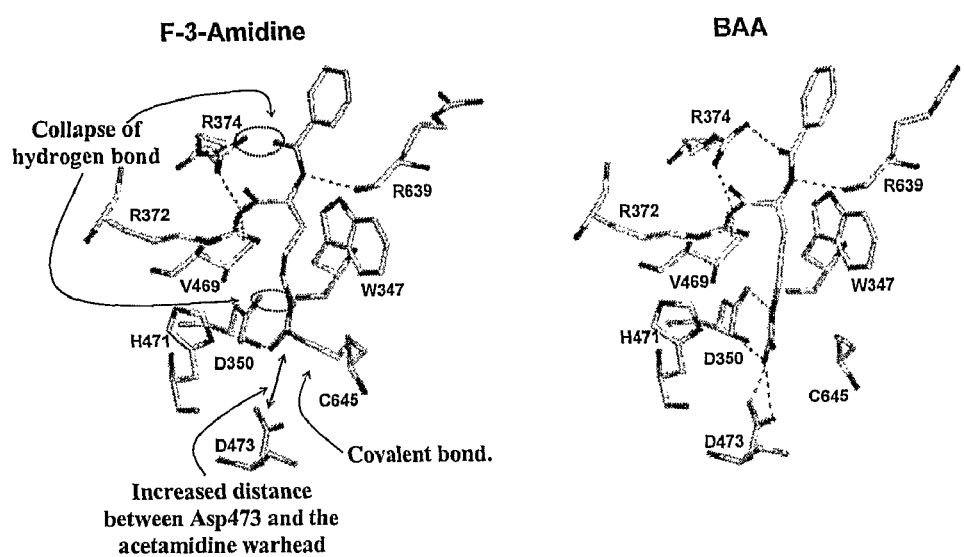
FIG. 14 illustrates a structural comparison of the PAD4.Ca$^{2+}$.F3-amidine and the PAD4.Ca$^{2+}$.BAA complexes.

In addition to the presence of electron density for an ideal 1.63 Å Cη-Sβ covalent bond, comparisons of the structures bound to BAA and F3-amidine revealed subtle conformational changes in the side chain of F3-amidine relative to BAA. For example, in the PAD4.BAA.calcium complex, Asp350 hydrogen bonds with both Nξ and Nη1 of the guanidinium moiety; whereas in the PAD4-F3-amidine.calcium complex, Asp350 hydrogen bonds to only Nη1. Moreover, the distance between Asp473 and Nη1 and Nη2 of the guanidinium group is increased in the F3-amidine containing structure, resulting in the loss of the bifurcated hydrogen bond network observed in the PAD4.BAA.calcium complex (FIG. 14). The loss of these interactions between the enzyme and the acetamidine moiety are likely caused by differences in the torsion and dihedral angles of the warhead that result upon reaction with the active site Cys—the plane of the covalently bonded acetamidine moiety is roughly perpendicular to the plane of the guanidinium in the enzyme.substrate complex. These conformational changes are transmitted through the rest of the molecule and result in the loss of an additional hydrogen bond between the side chain guanidinium of Arg374 and the main chain carbonyl of F3-amidine-Arg374 hydrogen bonds to the two main chain carbonyls of the substrate in the PAD4.BAA.calcium complex.

Experimental Procedures

Inhibitor Synthesis (Halo)acetamidine-based PAD4 inactivators were readily synthesized using adaptations of previously described methodologies (FIG. 18). Briefly, the Fmoc group on the resin was first deprotected with 20% piperidine to generate a free amine. A diamino acid (Dab, Orn or Lys), with both amino groups protected, was attached to Rink Amide AM resin via standard uronium based coupling methods, i.e. the α-carboxylic acid group of the diamino acids were activated with HBTU and HOBt. After removal of the Fmoc protective group, the α-amino group was benzolated with benzoyl chloride. The Dde group was then removed with 2% hydrazine and the free side chain amine reacted with either ethyl-, ethyl-fluoro-, or ethyl-chloro-acetimidate hydrochloride to form the (halo)acetamidine, i.e. for the synthesis of compounds 2-9. The warheads in compounds 10 and 11 were generated by reacting the free amine with either fluoroacetic acid or chloroacetic acid and DIC (1,3-diisopropylcarbodiimide). The ethyl-, ethyl-fluoro-, or ethyl-chloro-acetimidates were derived from the corresponding acetonitrile derivatives by reacting these compounds with ethanol in acidified ether. Final compounds were cleaved from resin by a mixture of 95% TFA, 2.5% TIS and 2.5% $H_2O$, and purified on a reverse phase HPLC.

Structural Characterization of (Halo)Acetamidine-Based Inactivators

1. Compound 2 is N-α-benzoyl-$N^5$-(2-chloro-1-iminoethyl)-L-Orn amide (2, Cl-3-amidine). Compound 2 was synthesized by a similar procedure as for 1; see ref. [1]. $^1$HNMR (400 MHz, $CD_3OD$) δ (ppm): 7.79-7.37 (m, 5H), 4.56-4.52 (dd, 1H), 4.26 (s, 2H), 3.34-3.20 (m, 2H), 1.98-1.64 (m, 4H). $^{13}$CNMR (400 MHz, $CD_3OD$) δ (ppm): 176.46, 170.31, 164.68, 135.03, 133.08, 129.63, 128.53, 54.17, 43.53, 40.11, 30.37, 25.00. MS-ES$^+$: 311 (M+1)$^+$. HRMS ($C_{14}H_{20}ClN_4O_2^+$): calculated 311.1275, observed 311.1266. Elemental analysis ($C_{16}H_{20}ClF_3N_4O_4$): calculated C, 45.24%; H, 4.75%; F, 13.42%. found C, 43.04%; H, 4.67%, F, 13.50%. Lyophilization of Compound 2, after reverse phase HPLC purification, results in the formation of the TFA salt.

2. Compound 3 is N-α-benzoyl-$N^5$-(1-iminoethyl)-L-Orn amide (3, H-3-amidine). Compound 3 was synthesized by a similar procedure as for 1; see ref. [1]. $^1$HNMR (400 MHz, $D_2O$) δ (ppm): 7.71-7.42 (m, 5H), 4.43-4.39 (dd, 1H), 3.23-3.20 (t, 2H), 2.09 (s, 3H), 1.96-1.63 (m, 4H). $^{13}$CNMR (400 MHz, $CD_3OD$) δ (ppm): 176.68, 170.46, 166.33, 135.21, 133.20, 129.77, 128.68, 54.39, 43.21, 30.57, 25.35, 19.02. MS-ES$^+$: 277 (M+1)$^+$. HRMS ($C_{14}H_{21}N_4O_2^+$): calculated 277.1665 observed 277.1660.

3. Compound 4 is N-α-benzoyl-$N^4$-(2-fluoro-1-iminoethyl)-L-Dab amide (4, F-2-amidine). Compound 4 was synthesized by a similar procedure as for 1; see ref. [1]. $^1$HNMR (400 MHz, $CD_3OD$) δ (ppm): 7.93-7.47 (m, 5H), 5.35-5.24 (d, $^2J_{H-F}$=45.4 Hz, 2H), 4.71-4.67 (dd, 1H), 3.57-3.41 (m, 2H), 2.39-2.10 (m, 2H). $^{13}$CNMR (400 MHz, $CD_3OD$) δ (ppm): 176.13, 170.56, 164.87, 164.68 (($^2J_{C-F}$=19.7 Hz), 135.00, 133.28, 129.76, 128.82, 80.04, 78.26 ($^1J_{C-F}$=179.4 Hz), 52.50, 40.76, 31.12. $^{19}$FNMR (400 MHz, $CD_3OD$) δ (ppm): −158.09, −158.21, −158.33 ($^2J_{H-F}$=45.8 Hz). MS-ES$^+$: 281 (M+1)$^+$. HRMS ($C_{13}H_{18}FN_4O_2^+$): calculated 281.1414, observed 281.1404.

4. Compound 5 is N-α-benzoyl-$N^4$-(2-chloro-1-iminoethyl)-L-Dab amide (5, Cl-2-amidine). Compound 5 was synthesized by a similar procedure as for 1; see ref. [1]. $^1$HNMR (400 MHz, $CD_3OD$) δ (ppm): 7.92-7.46 (m, 5H), 4.70-4.67 (dd, 1H), 4.41 (s, 2H), 3.57-3.40 (m, 2H), 2.39-2.10 (m, 2H). $^{13}$CNMR (400 MHz, $CD_3OD$) δ (ppm): 176.09, 170.56, 165.05, 135.00, 133.27, 129.76, 128.83, 52.55, 41.37, 40.30, 30.95. MS-ES$^+$: 297 (M+1)$^+$. HRMS ($C_{13}H_{18}ClN_4O_2^+$): calculated 297.1118, observed 297.1119.

5. Compound 6 is N-α-benzoyl-$N^4$-(1-iminoethyl)-L-Dab amide (6, H-2-amidine). Compound 6 was synthesized by a similar procedure as for 1; see ref [1]. $^1$HNMR (400 MHz, $CD_3OD$) δ (ppm): 7.92-7.46 (m, 5H), 4.70-4.67 (dd, 1H), 3.48-3.33 (m, 2H), 2.39-2.07 (m, 2H), 2.23 (s, 3H). $^{13}$CNMR (400 MHz, $CD_3OD$) δ (ppm): 176.21, 170.54, 166.61, 135.04, 133.24, 129.75, 128.81, 52.61, 40.80, 31.10, 19.15. MS-ES$^+$: 263 (M+1)$^+$. HRMS ($C_{13}H_{19}N_4O_2^+$): calculated 263.1508, observed 263.1496.

6. Compound 7 is N-α-benzoyl-$N^6$-(2-fluoro-1-iminoethyl)-L-Lys amide (7, F-4-amidine). Compound 7 was synthesized by a similar procedure as for 1; see ref. [1]. $^1$HNMR (400 MHz, CD$_3$OD) δ (ppm): 7.88-7.45 (m, 5H), 5.28-5.17 (d, $^2J_{H-F}$=45.4 Hz, 2H), 4.60-4.57 (dd, 1H), 3.35-3.32 (t, 2H), 2.02-1.80 (m, 2H), 1.78-1.65 (m, 2H), 1.61-1.43 (m, 2H). $^{13}$CNMR (400 MHz, CD$_3$OD) δ (ppm): 177.12, 170.39, 164.39, 164.20 ($^2J_{C-F}$=19 Hz), 135.30, 133.14, 129.76, 128.67, 79.98, 78.21 ($^1J_{C-F}$=179 Hz), 54.81, 43.48, 32.81, 28.23, 24.40. $^{19}$FNMR (400 MHz, CD$_3$OD) δ (ppm): −157.90, −158.03, −158.15 ($^2J_{H-F}$=45.8 Hz). MS-ES$^+$: 309 (M+1)$^+$. HRMS (C$_{15}$H$_{22}$FN$_4$O$_2^+$): calculated 309.1727, observed 309.1727.

7. Compound 8 is N-α-benzoyl-N$^6$-(2-chloro-1-iminoethyl)-L-Lys amide (8, Cl-4-amidine). Compound 8 was synthesized by a similar procedure as for 1; see ref. [1]. $^1$HNMR (400 MHz, D$_2$O) δ (ppm): 7.71-7.42 (m, 5H), 4.42-4.38 (dd, 1H), 4.24 (s, 2H), 3.27-3.24 (t, 2H), 1.92-1.70 (m, 2H), 1.69-1.55 (m, 2H), 1.51-1.34 (m, 2H). $^{13}$CNMR (400 MHz, CD$_3$OD) δ (ppm): 177.08, 170.38, 164.71, 135.29, 133.14, 129.76, 128.68, 54.78, 44.00, 40.24, 32.82, 28.11, 24.41. MS-ES$^+$: 325 (M+1)$^+$. HRMS (C$_{15}$H$_{22}$ClN$_4$O$_2^+$): calculated 325.1431, observed 325.1432.

8. Compound 9 is N-α-benzoyl-N$^6$-(1-iminoethyl)-L-Lys amide (9, H-4-amidine). Compound 9 was synthesized by a similar procedure as for 1; see ref. $^1$HNMR (400 MHz, CD$_3$OD) δ (ppm): 7.88-7.45 (m, 5H), 4.60-4.57 (dd, 1H), 3.25-3.22 (t, 2H), 2.17 (s, 3H), 2.00-1.76 (m, 2H), 1.74-1.64 (m, 2H), 1.60-1.44 (m, 2H). $^{13}$CNMR (400 MHz, CD$_3$OD) δ (ppm): 176.96, 170.22, 166.04, 135.17, 132.99, 129.61, 128.51, 54.65, 43.39, 32.68, 28.13, 24.31, 18.82. MS-ES$^+$: 291 (M+1)$^+$. HRMS (C$_{15}$H$_{23}$N$_4$O$_2^+$): calculated 291.1821, observed 291.1812.

9. Compound 10 is N-α-benzoyl-N$^5$-(2-fluoroacetyl)-L-Orn amide (10). Compound 10 was synthesized by a similar procedure as for 1; see ref. [1]. $^1$HNMR (400 MHz, CD$_3$OD) δ (ppm): 7.80-7.30 (m, 5H), 4.76-4.62 (d, 2H, $^2J_{H-F}$=47.0 Hz), 4.48-4.43 (dd, 1H), 3.27-3.16 (m, 2H), 1.89-1.68 (m, 2H), 1.62-1.50 (m, 2H). $^{13}$CNMR (400 MHz, CD$_3$OD) δ (ppm): 177.01, 170.70, 170.52, 170.34, 135.24, 132.90, 129.57, 128.55, 81.94, 80.12, 54.67, 39.41, 30.52, 27.15. $^{19}$FNMR (400 MHz, CD$_3$OD) δ (ppm): −53.62, −53.74, −53.87 ($^2J_{H-F}$=47.0 Hz). MS-ES$^+$: 296 (M+1)$^+$.

10. Compound 11 is N-α-benzoyl-N$^5$-(2-chloroacetyl)-L-Orn amide (11). Compound 11 was synthesized by a similar procedure as for 1; see ref. [1]. $^1$HNMR (300 MHz, CD$_3$OD) δ (ppm): 7.86-7.44 (m, 5H), 4.61-4.56 (dd, 1H), 4.02 (s, 2H), 3.35-3.21 (m, 2H), 2.01-1.76 (m, 2H), 1.73-1.62 (m, 2H). $^{13}$CNMR (400 MHz, CD$_3$OD) δ (ppm): 176.95, 170.31, 169.45, 135.26, 132.88, 129.55, 128.54, 54.63, 43.18, 40.28, 30.52, 27.02. MS-ES$^+$: 312 (M+1)$^+$.

IC$_{50}$ Assays

IC$_{50}$'s for compounds 2 to 11 were determined analogously to the methods used to determine the IC$_{50}$ for F3-amidine, 1. Briefly, inhibitors were pre-incubated with PAD4 (0.2 μM) for 15 min at 37° C. in a buffer containing 100 mM HEPES, pH 7.6, 50 mM NaCl, 10 mM CaCl$_2$, and 0.25 mM TCEP. BAEE was then added to a final concentration of 10 mM to initiate the reaction. Reactions were then quenched after a further 15 min by flash freezing. The amount of Cit produced in the reaction was quantified using our assay for Cit production. IC$_{50}$ values were determined by fitting the concentration-response data to Equation 3, $$\text{Fractional activity of PAD4} = 1/(1+([I]/IC_{50})) \quad \text{(Eq. 3)},$$

using the Grafit™ version 5.0.11 software package. The concentration of an inhibitor that corresponds to the midpoint (fractional activity=0.5) is referred to as the IC$_{50}$. The calcium dependence of the IC$_{50}$ was determined identically, except that CaCl$_2$ was omitted during the initial pre-incubation step and then added (10 mM final) with BAEE to initiate the reaction.

Time Course Assays

To initially evaluate the inhibitory properties of compounds H2-, H3-, and H4-amidine, progress curves were generated. For these experiments, inhibitors were pre-incubated for 10 minutes at 37° C. in assay buffer containing 2 mM BAEE. Reactions were then initiated by addition of PAD4 to a final concentration of 0.2 μM. At various time points, a 60 μl aliquot was withdrawn from an individual reaction, enzyme activity quenched by flash freezing, and the amount of Cit produced quantified. The data obtained for H3-, H2-, and H4-amidine were fit to a simple linear equation. For Cl3-amidine, values for k$_{inact}$, K$_I$ and k$_{inact}$/K$_I$ were obtained by multiplying the apparent k$_{obs.app}$'s by the transformation (1+[S]/K$_m$) to obtain the pseudo-first-order rate constant, k$_{obs}$, and these values were plotted versus inhibitor concentrations and fit to Equation 2, using the GraFit™ version 5.0.11 software package.

Rapid Dilution Time Course Assays

In order to determine whether F2-, F4-, Cl2-, Cl3-, and Cl4-amidine are irreversible PAD4 inactivators, rapid dilution time course experiments were performed to test for the recovery of enzymatic activity after rapidly diluting pre-formed enzyme-inactivator complexes 100-fold for F2-, F4-, Cl2- and Cl4-amidine and 95-fold for Cl3-amidine into assay buffer. For these experiments, the pre-formed enzyme-inactivator complex was generated by incubating PAD4 (10 μM for F2-, F4-, Cl2-, and Cl4-amidine, 9.5 μM for Cl3-amidine) with F2-, F4-, Cl2-, Cl3-, and Cl4-amidine (6 mM for F2-, F4- and Cl2-amidine, 167 μM for Cl3-amidine and 3 mM for Cl4-amidine) at 37° C. for 30 minutes. Reactions were then initiated by adding 6 μL (for F2-, F4-, Cl2- and Cl4-amidine) and 6.3 μL (for Cl3-amidine) of the pre-formed complex into a reaction buffer containing 10 mM BAEE (final volume 600 μL). At various time points (0, 2, 4, 6, 10, 15 minutes) 60 μL of the reaction was withdrawn and quenched by flash freezing in liquid nitrogen. Cit production was then quantified according to previously established methodologies.

Dialysis Experiments

To verify that Cl3-amidine is an irreversible PAD4 inactivator, pre-formed enzyme-Cl3-amidine complexes were generated and then dialyzed against 20 mM Tris-HCl, pH 8.0, 1 mM EDTA, 500 mM NaCl, 1 mM DTT, and 10% glycerol. Aliquots were taken at 0, 3.5, and 20 hours and the activity present in these samples quantified. Control reactions were treated identically.

H3-Amidine Inhibition Assays

Initial rates were determined in the absence and presence of various amounts of H3-amidine (0, 5, 10 mM), using BAEE as the substrate. BAEE and H3-amidine were pre-incubated in assay buffer containing 100 mM HEPES, pH 7.6, 50 mM NaCl, 0.5 mM TCEP, and 10 mM CaCl$_2$ for 10 min at 37° C. Reactions were initiated by the addition of PAD4 to a final concentration of 0.2 μM. After incubation at 37° C. for 15 min, the reactions were quenched and the amount of Cit produced quantified. The initial rates derived from these experiments were fit by non-linear least fit squares to equations representing linear competitive inhibition (Equation 4) and linear noncompetitive inhibition (Equation 5), using the using the GraFit™ version 5.0.11 software package.

$$v = V_m[S]/(K_m(1+[I]/K_{is})+[S]) \quad \text{(Eq. 4)}$$

$$v = V_m[S]/(K_m(1+[I]/K_{is})+[S](1+[I]/K_{ii})) \quad \text{(Eq. 5)}$$

$K_{ii}$ represents $K_i$ intercept and $K_{is}$ represents $K_i$ slope. Comparisons of the standard errors derived from fits of the data to Equations 4 and 5 are most consistent with H3-amidine being a competitive inhibitor.

In Vivo Studies

Transient transfection assays were performed analogously to previously described methods. Briefly, CV-1 cells were grown as previously described in 12-well dishes in DMEM media with 10% FBS. Plasmids encoding the GK1 luciferase reporter construct (125 ng), the p300 GBD fused to the Gal4 DNA Binding Domain (250 ng), the p300 binding domain of GRIP1 fused to the VP16 Activation Domain (AD) (250 ng), and either wild type or a catalytically defective C645S mutant (250 ng each) were transfected into CV-1 cells using Targefect (Targeting Systems, Santee, Calif.) according the manufacturer's protocol. Transfections were allowed to proceed for 3 hours, at which point, the media was removed and replaced with fresh DMEM, 10% FBS, and various concentrations of Cl3-amidine (0 to 200 µM). Luciferase activity present in cell extracts was then quantified after 40 hours.

Structural Studies

Crystals of F3-amidine in complex with wild type PAD4 were prepared by soaking this compound into previously prepared crystals of wild type PAD4. Crystals of the wild type enzyme were prepared according to previously established methods. Subsequently, these crystals were transferred to fresh crystallization buffer (0.1 M Imidazole (pH 8.0), 0.2 M $Li_2SO_4$, 10% PEGMME) containing 5 mM $CaCl_2$ and 5 mM F3-amidine for 8 hours. Diffraction data was then collected on BL41XU at SPring-8, indexed, and then scaled using the program HKL2000. Crystallographic data are shown in Table 3. The initial structure of the PAD4-F3-amidine.calcium complex was derived from the atomic coordinates of the PAD4C645A.BAA.calcium complex (Protein Bank ID code 1WDA). The structure was refined at the resolution of 2.3 Å using the program CNS and manual construction was performed using the graphic program O. At this stage, the F3-amidine moiety in the complex was identified on the $|F_o|-|F_c|$ maps. The structure was further refined by simulated annealing, energy minimization, and B-individual using the program CNS and finally converged after several further cycles of refinement with the program REFMAC. The final refinement statistics are given in Table 3.

Discussion

The putative role of human PAD4 in RA, a chronic disabling disease affecting ~1% of the worldwide population, prompted efforts to take a target-based approach to the development of PAD4-targeted RA therapeutics. As a part of this ongoing program, F3-amidine, a highly potent and bioavailable irreversible inactivator of PAD4 has been designed, synthesized, and evaluated. To gain insights into the importance of warhead positioning and the identity of the leaving group, a series of 8 analogs have been synthesized that differed in both side chain length and the identity of the leaving group and characterized their inhibitory properties.

The results of the studies clearly indicate that both factors are determinants of inactivator potency. For example, the fact that F2-, F4-, Cl2-, and Cl4-amidine are significantly poorer inhibitors than either F3- or Cl3-amidine is consistent with the idea that the correct positioning of the warhead can be important for inactivation. The decreased potency observed for F4- and Cl4-amidine is believed to be the result of a reduction in affinity for these inactivators because the side chains are too long, which results in disruptions to the hydrogen bond network that is formed between the backbone of the inactivator and the main-chain carbonyl of Arg639 and the guanidinium group of Arg374. In contrast, the relative lack of potency observed for Cl2-amidine is likely due to the inability to correctly position the warhead for optimal reaction with the active site Cys, while maintaining the aforementioned hydrogen bonding network.

The role of warhead positioning in inactivator potency is also highlighted by the fact that Cl2-amidine is an irreversible inactivator, whereas F2-amidine is not, suggesting that the correct orientation of the fluoroacetamidine warhead, relative to the active site Cys, can be desired for the reaction of this warhead with this residue. These results are consistent with the initial hypothesis that fluoroacetamidines inactivate PAD4 via an initial attack on the iminium carbon to form a tetrahedral intermediate that evolves into a three-membered sulfonium ring prior to its rearrangement to form the thioether observed in the structure of the PAD4-F3-amidine.calcium complex. In contrast, the fact that Cl2-amidine is an irreversible inactivator, combined with the expected increase in distance between Cys645 and the chloroacetamidine warhead, suggest that this compound inactivates PAD4, albeit with reduced efficiency, via the direct displacement of the halide, i.e. Mechanism 1 in FIG. 9. In total, these results demonstrate the importance of positioning to inactivator potency and indicate that the correct position of a warhead can be taken into account during the design of inhibitors with improved potency. This can be especially important for compounds containing a fluoroacetamidine warhead.

The results described herein also highlight the key desirability for an electron-withdrawing leaving group. For example, the fact that H2-, H3-, and H4-amidine are reversible inhibitors demonstrates that reaction with the active site thiolate may requires an electron-withdrawing group to enhance the electrophilicity of the iminium carbon. The lack of potency observed for these compounds also reveals the inherent challenges in developing reversible inhibitors targeting this enzyme; thereby providing a strong rationale for the use of the haloacetamidine-based warhead in the development of a PAD4-targeted therapeutic.

The identity of the leaving group can also play an important role in inactivator potency. For example, Cl2-amidine is significantly more potent than F2-amidine. The higher potency observed for Cl2-amidine is likely a reflection of the fact that chloride is a better leaving group than fluoride. Consistent with these results is the finding that Cl3-amidine is a significantly, for example about 4-fold, more potent inactivator than F3-amidine. Again, this likely reflects the greater leaving group potential of chloride. However, it is interesting to note that the increase in potency does not fully reflect the greater than $10^5$-fold difference in leaving group potential. The lack of a more significant effect may reflect the larger size of the chloro group, which could sterically hinder optimum reaction with the active site thiolate. Consistent with such a possibility is the fact that methylated Arg residues are very poor in vitro substrates for PAD4, presumably because the added bulk of the methyl group prevents the guanidinium group from adopting an orientation that maximizes its reaction with the active site Cys. Thus, the lack of a more significant improvement in inhibitor potency may be due to an improperly oriented warhead.

Although structural studies with F3-amidine have demonstrated that this compound specifically modifies Cys645, the identification of the residue modified by Cl3-amidine has remained elusive—structural and mass spectrometry experiments have failed to definitively identify the residue modified by the latter compound. However, these results with F3-amidine, combined with the Fast group's finding that 2-chloroacetamidine modifies the active site Cys in DDAH, strongly suggests that Cl3-amidine inactivates PAD4 via the modification of Cys645. The modification of this active site residue is further supported by the fact that inactivation is substrate and calcium dependent.

As noted above, the calcium dependence of inactivation likely arises because PAD4 is a calcium dependent enzyme that undergoes a conformational change upon binding to this metal ion such that Cys645 and His471 are moved into positions that are competent for catalysis and reaction with these inactivators. From a therapeutic standpoint, this discovery is highly significant because it suggests that compounds bearing either the fluoro- or chloro-acetamidine warhead would preferentially modify the activated form of the enzyme; thereby limiting the toxicity that might be expected to result if both the active and inactive forms of the enzyme were to be inactivated. The ability to preferentially modify the active form of the enzyme should also facilitate the development of biotin-tagged activity-based protein profiling reagents that can be used to selectively enrich for the active form of the enzyme and thereby identify the numbers and types of post-translational modifications that this enzyme undergoes in vivo. These latter experiments are significant because they help identify the signaling pathways in which PAD4 participates and give clues as to how dysregulation of PAD4 can give rise to RA.

Example 3

F-amidine ($k_{inact}/K_I$ of 3000 $M^{-1}min^{-1}$) and Cl-amidine ($k_{inact}/K_I$ of 13000 $M^{-1}min^{-1}$) are the most potent PAD4 inhibitors to be described to date and are significantly more potent than 2-chloro-acetamidine ($k_{inact}/K_I$=35 $M^{-1}min^{-1}$). The increased potency is likely due to the binding energy gained by the addition of the benzoylated ornithine moiety that targets these inhibitors to the PAD4 active site.

In addition to their high potency, ease of synthesis, and ability to irreversibly modify PAD4, the fact that F- and Cl-amidine inactivate PAD4 in a calcium dependent manner led us to consider that these compounds could be adapted for use as activity based protein profiling reagents (ABPPs). Herein, is described the design, synthesis, and evaluation of two fluorescently tagged PAD4 inactivators, rhodamine-tagged F-amidine (RFA; 3) and rhodamine-tagged Cl-amidine (RCA; 4), that preferentially label the active, i.e. calcium bound, form of the enzyme.

During the design of these fluorescently-tagged ABPPs, a triazole linker was used because it is readily generated via the copper(I)-catalyzed azide-alkyne [3+2]cycloaddition reaction and because it affords a level of versatility that is not provided by other linkers, i.e. the fluorescent tag can be added in a bio-orthogonal manner either before or after the inactivator has undergone reaction with the protein of interest.

The synthesis of RFA and RCA, which is described in detail herein, utilizes a solid phase synthetic methodology that involves the on-resin coupling of an ethyl haloacetimidate hydrochloride to N-α-4-azidobenzoyl ornithine (Scheme S1—FIG. 24). Subsequently, this compound is cleaved from the resin and can be coupled to a previously described rhodamine-alkyne construct via the copper(I)-catalyzed azide-alkyne [3+2]cycloaddition reaction and then purified by reverse phase HPLC.

Figure 20:
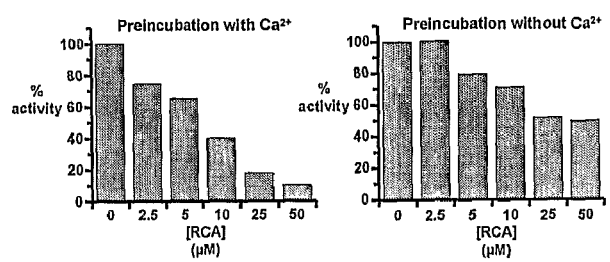
FIG. 20 illustrates representative IC50 data determined with and without preincubation with calcium.

To evaluate the inhibitory properties of RFA and RCA, $IC_{50}$'s were determined using previously established methods. Briefly, the compounds were pre-incubated with PAD4 in the absence or presence of $Ca^{2+}$ for about 15 minutes prior to assaying (FIG. 20). The $IC_{50}$'s of RFA and RCA have been found to be 23.7±4.1 µM and 7.4±0.8 µM, respectively, when preincubated with $Ca^{2+}$ versus >76 µM and >50 µM when preincubated in the absence of $Ca^{2+}$. These results are consistent with previous results demonstrating that F- and Cl-amidine are $Ca^{2+}$-dependent inactivators of PAD4. Remarkably the $IC_{50}$'s for both RFA and RCA are comparable to those obtained for F-amidine (21.6±2.1 µM) and Cl-amidine (5.9±0.3 µM); thereby indicating that the reporter tag does not influence the interaction between these compounds and PAD4.

Figure 21:
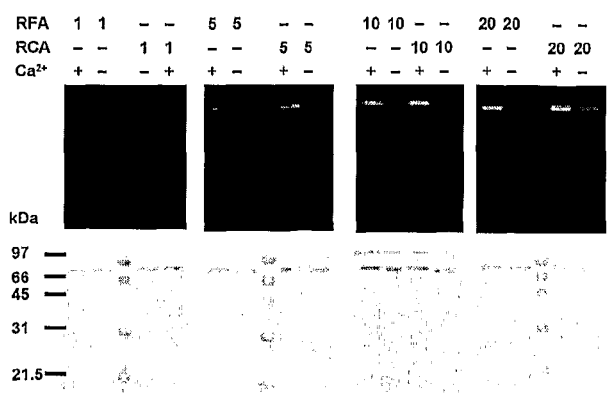
FIG. 21 illustrates in vitro labeling of PAD4 with RFA and RCA.

Having established that RFA and RCA inhibit PAD4 with comparable potency to their parent compounds, their ability to act as ABPPs was evaluated by incubating them with PAD4 in the absence and presence of $Ca^{2+}$. The reaction components were then separated on a 12% SDS-PAGE gel and fluorescently labeled proteins visualize (FIG. 21). The results of these studies clearly demonstrate that RFA and RCA preferentially modify the active form of the enzyme, i.e. calcium bound PAD4; although it should be noted that at higher concentrations of RCA, PAD4 is modified in the absence of calcium. In contrast, a C645S mutant, which lacks the active site nucleophile and is essentially inactive, is not modified by RFA and only minimally modified by RCA (FIG. 23), consistent with crystallographic and mass spectrometry experiments demonstrating that this is the residue modified in PAD4. MALDI-MS experiments on full-length PAD4 treated with RFA and RCA show respective mass shifts of 937 and 956 Da relative to control samples, consistent with the preferential modification of a single site, i.e., Cys645, on the enzyme. Limit of detection assays demonstrate that as little as ~0.6 µg of PAD4 can be readily detected with either RFA or RCA.

Figure 22:
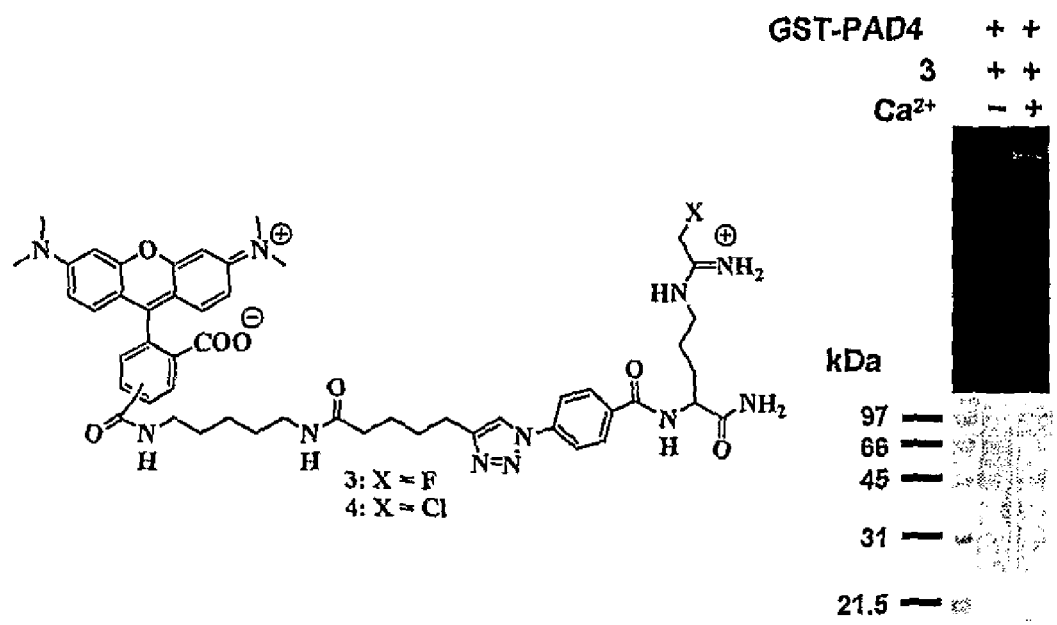
FIG. 22 illustrates fluorescently labeled proteins on a 12% SDS-PAGE gel.

To evaluate the abilities of RFA and RCA to act as ABPPs in a complex protein mixture, E. coli cell extracts were prepared overexpressing either wild type PAD4 or the C645S mutant and were then incubated with either RFA or RCA in the presence or absence of $Ca^{2+}$. The reaction components were separated on a 12% SDS-PAGE gel and fluorescently labeled proteins were visualized (FIG. 22). Remarkably, RFA and RCA were highly selective for the calcium bound form of wild type but not mutant PAD4; thereby demonstrating that these ABPPs can readily label PAD4 even in the presence of highly complex cellular mixtures.

The ability of RCA, and in particular RFA, to preferentially label the active form of PAD4 indicates that these compounds are powerful small molecule chemical probes that may be useful for deciphering the normal and pathophysiological roles of this enzyme and how (or if) dysregulation of these pathways contributes to the onset and progression of RA. Additionally, these fluorescently tagged ABPPs can be useful for identifying the in vivo conditions under which this enzyme is activated and help to determine if post-translational modifications, e.g. proteolytic processing, occur to this enzyme during its in vivo activation. Furthermore, these probes may prove to be useful RA diagnostics and will undoubtedly aid the identification of non-specific targets of these compounds whose identities will aid the successful design and synthesis of PAD4-specific inhibitors. In addition, the fact that compounds incorporating the fluoroacetamidine warhead are more selective for the calcium bound, i.e. active, form of the enzyme suggests that future iterations of these compounds may have better pharmacological characteristics than chloroacetamidine containing compounds because they are likely to be more selective for PAD enzymes and would therefore be expected to have fewer off target effects.

Synthesis of 6-heptynoic acid succinimidyl ester (6)

6-heptynoic acid (5) (≧97%, TCI, Portland, Oreg.) (1 g, 7.9 mmol, 1 equiv.) was dissolved in 100 ml of anhydrous methylene chloride. N-hydroxysuccinimide (NHS) (98+%, Acros, New Jersey) (2.3 g, 19.8 mmol, 2.5 equiv.) and 1-(3-dimethylaminopropyl)-3-ethylcarbodiimide hydrochloride (EDC) (98+%, Alfa Aesar) (2.3 g, 11.9 mmol, 1.5 equiv.) was added to the above solution. The resulting reaction mixture was stirred at room temperature overnight (18 hours) before 500 ml of a saturated sodium bicarbonate aqueous solution was added to it. The aqueous phase was extracted with 500 ml of ether. The ether extract was combined with the methylene chloride phase, washed with 500 ml of water and 500 ml of brine, and then dried with anhydrous magnesium sulfate. After magnesium sulfate was filtered away and the solvent was removed by rotary evaporation, an off-white solid (1.3 g, 72% yield) was obtained after being further dried overnight under vacuum. This solid was then used directly in the next step.

Synthesis of 6-heptynoic acid (5-amino-pentyl)-amide hydrogen chloride (8)

N-1-Boc-1,5-diaminopentane hydrogen chloride (7) (>99%, BACHEM, Torrance, Calif.) (215 mg, 0.9 mmol, 2 equiv.) was dissolved in 20 ml of anhydrous methanol. To this solution 0.2 ml of dry triethylamine (1.35 mol, 3 equiv.) was added and the reaction mixture was stirred at room temperature for 15 minutes before 6-heptynoic acid succinimidyl ester (6) (100 mg, 0.45 mmol, 1 equiv.) was added. After the reaction proceeded for 3 hours, the solvent was removed by rotary evaporation and the resulting crude product was dried under vacuum for 2 hours. Purification by column chromatography (neutral alumina, $CHCl_3$/MeOH (98%/2%)) afforded a Boc-protected form of 8—6-heptynoic acid (5-(Boc)amino-pentyl)-amide (80 mg, 57% yield). (MS-ES$^+$: m/z 311 (M+1)).

The Boc-protected form of 8 was dissolved in 20 ml of 4 N HCl in 1,4-dioxane and the resulting reaction solution was stirred at room temperature for 5 hours. After the solvent was evaporated away under $N_2$ flow, 8 (48 mg, 75% yield) was obtained after being further dried under vacuum overnight (18 hours) and used directly in the next step. $^1$HNMR (300 MHz, $CD_3OD$) δ (ppm): 3.35-3.30 (t, 2H), 2.97-2.92 (t, 2H), 2.48-2.43 (t, 2H), 2.26-2.23 (t, 2H), 1.82-1.44 (m, 11H). $^{13}$CNMR (300 MHz, $CD_3OD$) δ (ppm): 176.581, 83.263, 69.023, 40.254, 39.436, 34.143, 27.969, 27.902, 26.892, 25.121, 23.551, 17.563. MS-ES$^+$: m/z 211 (M+1). HRMS ($C_{12}H_{23}N_2O^+$): calculated 211.1810, observed 211.1812.

Synthesis of 6-heptynoic acid (5-(5(6)-TAMRA amido-pentyl)-amide (10)

5-(and -6)-carboxytetramethylrhodamine succinimidyl ester (9) (>95%, AnaSpec., San Jose, Calif.) (25 mg, 0.047 mmol, 1 equiv.) in 0.5 ml of dry N,N-dimethylformamide was added to 8 (40 mg, 0.16 mmol, 3.4 equiv.) in 0.1 ml of dry N,N-dimethylformamide. Triethylamine was then added (0.03 ml, 0.21 mmol, 4.4 equiv.). This reaction solution was stirred at room temperature overnight (18 hours). Purification by column chromatography (neutral alumina, $CHCl_3$/MeOH (90%/10%)) afforded 10 (14 mg, 48% yield) as a dark pink solid. $^1$HNMR (400 MHz, $CDCl_3$) δ ppm): 8.40 (s, 1H), 8.15 (d, 1H), 8.13 (d, 1H), 7.99-7.93 (q, 2H), 7.47 (s, 1H), 7.19 (s, 2H), 7.04-7.02 (t, 1H), 6.55-6.54 (d, 2H), 6.53-6.52 (d, 2H), 6.42-6.40 (t, 4H), 6.35-6.34 (t, 2H), 6.33-6.32 (t, 2H), 5.77-5.71 (m, 2H), 3.43-3.39 (q, 2H), 3.31-3.26 (q, 2H), 3.18-3.11 (m, 4H), 2.92 (m, 24H), 2.12-2.03 (m, 9H), 1.88-1.87 (t, 1H), 1.85-1.84 (t, 1H), 1.68-1.57 (m, 7H), 1.52-1.41 (m, 12H), 1.39-1.18 (m, 8H), 0.87-0.80 (m, 3H). $^{13}$CNMR (400 MHz, $CDCl_3$) δ (ppm): 173.01, 172.89, 169.20, 169.04, 166.18, 153.17, 153.04, 152.43, 152.32, 140.50, 136.32, 134.10, 130.25, 128.91, 128.82, 128.49, 125.30, 124.79, 123.21, 122.80, 108.97, 108.93, 106.47, 106.43, 98.44, 98.42, 84.15, 84.10, 68.66, 68.61, 66.82, 40.27, 39.98, 38.97, 38.74, 36.12, 36.09, 34.02, 30.42, 29.19, 29.14, 28.93, 28.80, 28.76, 27.96, 27.91, 24.89, 24.84, 24.49, 23.87, 23.84, 23.80, 22.97, 18.18, 14.05, 10.99. MS-ES$^+$: m/z 623 (M+1). HRMS ($C_{37}H_{43}N_4O_5^+$): calculated 623.3233, observed 623.3240

Synthesis of N-α-(4-azido)benzoyl-N$^5$-(2-fluoro-1-iminoethyl)-L-ornithine amide (11) and N-α-(4-azido)benzoyl-N$^5$-(2-chloro-1-iminoethyl)-L-ornithine amide (12)

The synthesis procedure is similar to that reported before.[12]

N-α-(4-azido)benzoyl-N$^5$-(2-fluoro-1-iminoethyl)-L-ornithine amide (11): $^1$HNMR (400 MHz, $CD_3OD$) δ (ppm): 7.83-7.81 (d, 2H), 7.08-7.06 (d, 2H), 5.21-5.10 (d, $^2J_{H-F}$=45.4 Hz, 2H), 4.53-4.50 (dd, 1H), 3.34-3.28 (m, 2H), 1.93-1.67 (m, 4H). $^{13}$CNMR (400 MHz, $CD_3OD$) δ (ppm): 176.49, 169.24, 164.42-164.23 ($^2J_{C-F}$=20 Hz), 145.32, 131.48, 130.51, 120.02, 79.86-78.08 ($^1J_{C-F}$=180 Hz), 54.23, 42.98, 30.33, 25.13. $^{19}$FNMR (400 MHz, $CD_3OD$) δ (ppm): −158.01, −158.13, −158.25 ($^2J_{H-F}$=45.3 Hz). MS-ES$^+$: m/z 336 (M+1). HRMS ($C_{14}H_{19}FN_7O_2^+$): calculated 336.1584, observed 336.1587. N-α-(4-azido)benzoyl-N$^5$-(2-chloro-1-iminoethyl)-L-ornithine amide (12): $^1$HNMR (400 MHz, $D_2O$) δ (ppm): 7.74-7.72 (d, 2H), 7.10-7.08 (d, 2H), 4.45-4.41 (dd, 1H), 4.33 (s, 2H), 3.35-3.32 (t, 2H), 1.99-1.64 (m, 4H). $^{13}$CNMR (400 MHz, $D_2O$) δ (ppm): 176.44, 169.92, 162.74, 144.08, 129.14, 128.99, 119.06, 53.69, 41.99, 39.11, 28.17, 23.21. MS-ES$^+$: m/z 352 (M+1). HRMS ($C_{14}H_{19}ClN_7O_2^+$): calculated 352.1289, observed 352.1292.

Synthesis of RFA (3) and RCA (4)

Click reaction between 10 and 11 (or 12) was carried out in 15 ml of a reaction buffer composed of 10 (100 μM final, 1 equiv., 2 mM stock in 50 mM HEPES pH 7.6 buffer/$H_2O$/ EtOH (1/4/8 volume ratio), 11 (or 12) (200 μM final, 2 equiv., 2 mM stock in 50 mM HEPES pH 7.6 buffer), TCEP (25 μM final, 0.25 equiv.), ligand[13] (bathocuproinedisulphonic acid disodium salt hydrate) (97%, Alfa Aesar) (50 μM final, 0.5 equiv.) and copper sulfate (25 μM final, 0.25 equiv.) at 37° C. under nitrogen for 2 h. RFA and RCA were purified by reverse phase HPLC with quantitative yields. RFA (3): $^1$HNMR (400 MHz, $CD_3OD$) δ (ppm): 8.35 (s, 1H), 8.02-7.88 (m, 24H), 7.72-7.67 (q, 22H), 7.49-7.45 (t, 26H), 7.22-7.20 (d, 4H), 6.83-6.78 (q, 4H), 6.59-6.57 (d, 4H), 6.32-6.26 (d, 4H), 5.23 (d, 2H), 5.12 (d, 2H), 4.41-4.34 (m, 4H), 3.66 (s, 1H), 3.63-3.62 (d, 1H), 3.43-3.29 (m, 4H), 3.28 (s, 22H), 3.22-3.16 (m, 6H), 3.00 (s, 34H), 2.46-2.39 (m, 5H), 2.15 (s, 5H), 2.11-2.07 (t, 5H), 1.91-1.21 (m, 39H). MS-ES$^+$: m/z 480 (z=2). RCA (4): $^1$HNMR (400 MHz, $CD_3OD$) δ (ppm): 8.27 (s, 1H), 7.94-7.85 (m, 5H), 7.69-7.64 (q, 3H), 7.47-7.41 (q, 5H), 7.19-7.17 (d, 1H), 6.83-6.76 (m, 4H), 6.58-6.55 (t, 4H), 6.33-6.27 (d, 4H), 4.34-4.28 (t, 2H), 4.25 (d, 4H), 3.24 (s, 27H), 2.99 (s, 30H), 2.44-2.39 (q, 4H), 2.12 (s, 3H), 2.07 (s, 4H), 1.85-1.23 (m, 34H). MS-ES$^+$: m/z 488 (z=2).

In Vitro Labeling of Wild Type PAD4 with RFA and RCA 0.2 μM PAD4 (2.4 μg, 16 μl of 2 μM PAD4 in a long term storage buffer containing 20 mM Tris-HCl pH 7.6, 1 mM EDTA, 1 mM DTT, 10% (v/v) glycerol, and 500 mM NaCl was incubated in reaction buffer containing 50 mM HEPES pH 7.6, 0.23 mM TCEP and various concentrations of RXA (dissolved in 50 mM HEPES pH 7.6 buffer) in the presence or absence of 9 mM CaCl$_2$ for 1 h at 37° C. 5 µl of standard 6×SDS-PAGE loading buffer was added to each sample. Proteins were separated on a 12% SDS-PAGE electrophoresis gel and visualized in-gel using an ultraviolet transilluminator (Fisher Biotech).

In Vitro Labeling of the C645S mutant with RFA and RCA

The GST-tagged PAD4C645S mutant (5 µg) was incubated in a reaction buffer containing 50 mM HEPES pH 7.6, 0.25 mM TCEP and 50 µM RFA or RCA in the presence or absence of 10 mM CaCl$_2$ at 37° C. for 1 hour. Each sample was mixed with 5 µl of 6×SDS-PAGE loading buffer, heated at 90° C. for 10 minutes, run on a 12% SDS-PAGE and visualized in-gel using an ultraviolet transilluminator (Fisher Biotech).

In Vitro Labeling of E. coli with RFA and RCA

E. coli cell extracts (12.5 µg of total protein) overexpressing either GST-tagged PAD4 or the GST-tagged C645S mutant were incubated in a reaction buffer containing 50 mM HEPES pH 7.6, 0.25 mM TCEP and 50 µM RFA or RCA in the presence or absence of 10 mM CaCl$_2$ at 37° C. for 1 h. Each sample was mixed with 5 µl of 6×SDS-PAGE loading buffer, heated at 90° C. for 10 minutes, run on a 12% SDS-PAGE and visualized in-gel using an ultraviolet transilluminator.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only and is not intended to limit the disclosure so further described in such appended claims.

TABLE 1

Table 1: IC$_{50}$'s of Benzoylated Amidines[a]

| Compound Name | Compound Number | IC$_{50}$ (µM) |
|---|---|---|
| H-Amidine | 18 | 4300 ± 700 |
| F-Amidine | 21 | 19.9 ± 3.6 |
| Cl-Amidine | 24 | 7.1 ± 1.2 |

[a]IC$_{50}$'s were determined by pre-incubating the indicated inhibitor with PAD4 and Ca$^{2+}$ (10 mM) for 10 min and then initiating the reaction by adding BAEE (1 mM final). Assays were performed in duplicate for 20 minutes and IC$_{50}$'s determined by fitting the concentration-response data to: Fractional Activity = 1/(1 + ([I]/IC$_{50}$)).

TABLE 2

| Name | Compound No. | IC$_{50}$ (µM) |
|---|---|---|
| F3-amidine | 1 | 21.6 ± 2.1 |
| Cl3-amidine | 2 | 5.9 ± 0.3 |
| H3-amidine | 3 | >1000 |
| F2-amidine | 4 | >1000 |
| Cl2-amidine | 5 | 585 ± 65 |
| H2-amidine | 6 | >1000 |
| F4-amidine | 7 | 655 ± 100 |
| Cl4-amidine | 8 | 640 ± 10 |
| H4-amidine | 9 | >1000 |
| F3-acetamide[a] | 10 | >500 |
| Cl3-acetamide[a] | 11 | >500 |

IC$_{50}$ is the concentration of the inhibitor/inactivator that yields half maximal activity. IC$_{50}$'s were determined by preincubating PAD4 and the inhibitor/inactivator in the presence of 10 mM calcium for 15 min prior to the addition of 10 mM BAEE to initiate the enzyme assay. See Methods section for assay details.
[a]No inhibition was noted with these compounds even at the highest concentration tested. Higher concentrations could not be tested because of solubility issues.

TABLE 3

Table 3 Crystallographic data and Refinement statistics.

| Crystallographic data | |
|---|---|
| Space group | C2 |
| Cell dimension | a = 146.3 Å, b = 60.5 Å, c = 115.0 Å, = 124.2° |
| Resolution range (Å) | 50.00-2.30 |
| Total observation | 109,379 |
| Unique observation | 31,719 |
| Completeness (%) | 85.0 (47.6) |
| R$_{merge}$ (%) [1] | 3.4 (19.5) |
| <I/σ (I)> | 15.9 |
| Refinement statistics | |
| Resolution (Å) | 50.00-2.30 |
| R$_{work}$/R$_{free}$ (%) [2] | 19.8/25.4 |
| R.M.S. deviation | |
| Bond length (Å) | 0.017 |
| Bond angle (°) | 1.706 |
| Mean B value (Å$^2$) | 56.5 |

Values in parentheses are for the highest resolution shell.
[1] $R_{merge} = \Sigma_h \Sigma_i |I(h)_i - <I(h)>|/\Sigma_h \Sigma_i I(h)_i$
[2] $R_{work}/R_{free} = \Sigma ||F_o| - |F_c||/\Sigma |F_o|$, where R$_{work}$ and R$_{free}$ are calculated by using the working and free reflection sets, respectively. R$_{free}$ reflections (5% of the total) were held aside throughout refinement.

What is claimed:

1. An inactivator of protein arginine deiminase 4, said inactivator comprising:

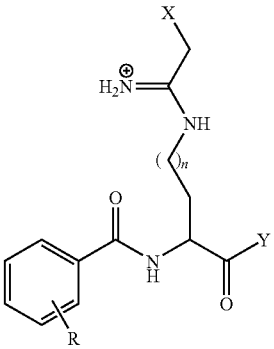

wherein x comprises F, Cl, or H;

wherein y comprises OH or NH$_2$;

wherein R comprises H, an alkyl group, an alkenyl group, or an alknyl group; and n is greater than 0.

2. The inactivator of claim 1, wherein x comprises F.

3. The inactivator of claim 1, wherein x comprises Cl.

4. The inactivator of claim 1, wherein the concentration of said inactivator that yields half-maximal activity of protein arginine deiminase 4 is less than about 50 µM.

5. The inactivator of claim 1, wherein the concentration of said inactivator that yields half-maximal activity of protein arginine deiminase 4 is less than about 25 µM.

6. The inactivator of claim 1, wherein the concentration of said inactivator that yields half-maximal activity of protein arginine deiminase 4 is less than about 10 µM.

7. An inactivator of protein arginine deiminase 4, said inactivator comprising

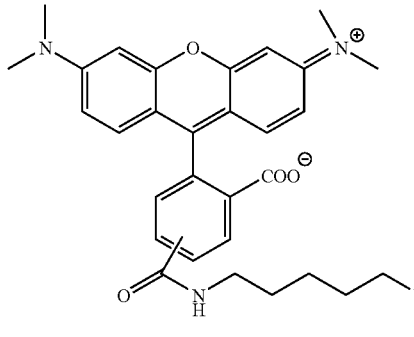

wherein x comprises F or Cl.

8. The inactivator of claim 7, wherein x comprises F.

9. The inactivator of claim 7, wherein x comprises Cl.

10. The inactivator of claim 7, wherein the concentration of said inactivator that yields half-maximal activity of protein arginine deiminase 4 is less than about 50 µM.

11. The inactivator of claim 7, wherein the concentration of said inactivator that yields half-maximal activity of protein arginine deiminase 4 is less than about 25 µM.

12. The inactivator of claim 7, wherein the concentration of said inactivator that yields half-maximal activity of protein arginine deiminase 4 is less than about 10 µM.

13. A method for inactivating protein arginine deiminase 4, said method comprising:

contacting protein arginine deiminase 4 with an inactivator;

said inactivator comprising

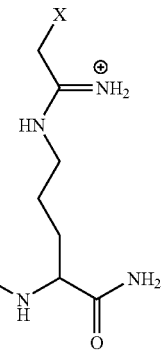

wherein x comprises F, Cl, or H; and
n is greater than 0.

14. A method as in claim 13, wherein said method is performed in vivo.

15. A method as in claim 13, wherein x comprises F.

16. A method as in claim 13, wherein x comprises Cl.

17. A method for inactivating protein arginine deiminase 4, said method comprising:

contacting protein arginine deiminase 4 with an inactivator;

said inactivator comprising

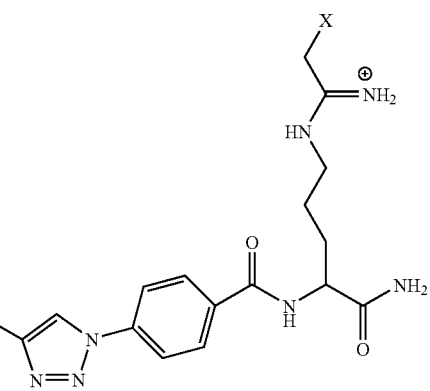

wherein x comprises F and or Cl.

18. A method as in claim 17, wherein said method is performed in vivo.

19. A method as in claim 17, wherein x comprises F.

20. A method as in claim 17, wherein x comprises Cl.

21. A method for synthesis of a protein arginine deiminase 4 inactivator, said method comprising:
   on-resin coupling of an acetimidate to an ornithine to form a compound; and
   cleaving said compound from said resin.

22. The method of claim 21, further comprising coupling said coupound to a rhodamine-alkyne construct.

23. The method of claim 21, wherein said acetimidate comprises ethyl haloacetimidate hydrochloride.

24. The method of claim 21, wherein said ornithine comprises N-α-4-azidobenzoyl ornithine.

* * * * *

UNITED STATES PATENT AND TRADEMARK OFFICE
CERTIFICATE OF CORRECTION

PATENT NO. : 7,964,636 B2
APPLICATION NO. : 12/092627
DATED : June 21, 2011
INVENTOR(S) : Thompson et al.

Page 1 of 2

It is certified that error appears in the above-identified patent and that said Letters Patent is hereby corrected as shown below:

In the Claims:

Column 29, line 1, please replace compound with the following:

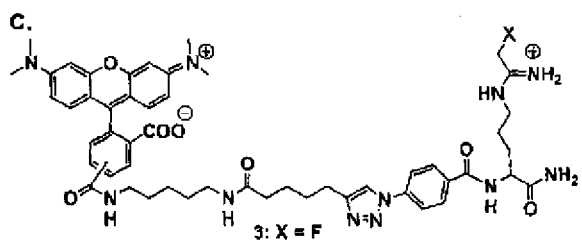

Column 30, line 23, please replace compound with the following:

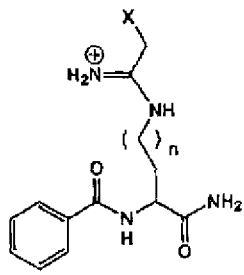

Across the bottom of columns 29 and 30, line 48, please replace compound with the following:

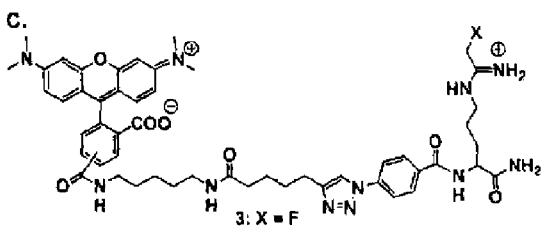

Signed and Sealed this
Second Day of July, 2013

Teresa Stanek Rea
*Acting Director of the United States Patent and Trademark Office*

Column 30, bottom line under compound after word "comprises F", please delete the word "and".